(12) United States Patent
Zhang et al.

(10) Patent No.: US 11,819,409 B2
(45) Date of Patent: Nov. 21, 2023

(54) ARTIFICIAL CHORDAE TENDINEAE IMPLANTATION SYSTEM AND CLAMP AIDING APPARATUS THEREOF

(71) Applicant: HANGZHOU VALGEN MEDTECH CO., LTD., Zhejiang (CN)

(72) Inventors: Tingchao Zhang, Zhejiang (CN); Weiwei Zhang, Zhejiang (CN); Chunyuan Zhou, Zhejiang (CN)

(73) Assignee: HANGZHOU VALGEN MEDTECH CO., LTD., Zhejiang (CN)

( * ) Notice: Subject to any disclaimer, the term of this patent is extended or adjusted under 35 U.S.C. 154(b) by 706 days.

(21) Appl. No.: 16/639,209

(22) PCT Filed: Aug. 15, 2018

(86) PCT No.: PCT/CN2018/100654
§ 371 (c)(1),
(2) Date: Oct. 20, 2020

(87) PCT Pub. No.: WO2019/034081
PCT Pub. Date: Feb. 21, 2019

(65) Prior Publication Data
US 2021/0045877 A1 Feb. 18, 2021

(30) Foreign Application Priority Data
Aug. 17, 2017 (CN) .......................... 20171078970.0

(51) Int. Cl.
*A61F 2/24* (2006.01)

(52) U.S. Cl.
CPC .......... *A61F 2/2457* (2013.01); *A61F 2/2466* (2013.01); *A61F 2230/0004* (2013.01)

(58) Field of Classification Search
CPC .... A61F 2/2457; A61F 2/2466; A61F 2/2454; A61B 2017/1125; A61B 2017/1132; A61B 17/1146; A61B 2018/145
See application file for complete search history.

(56) References Cited

U.S. PATENT DOCUMENTS

| 2004/0044365 A1* | 3/2004 | Bachman | A61B 17/0401 |
| | | | 606/213 |
| 2008/0195126 A1 | 8/2008 | Solem | |

(Continued)

FOREIGN PATENT DOCUMENTS

| CN | 102341063 A | 2/2012 |
| CN | 103347464 A | 10/2013 |

(Continued)

OTHER PUBLICATIONS

Extended European Search Report dated Apr. 8, 2021 in corresponding European Patent Application No. 18845642.0.

(Continued)

*Primary Examiner* — Sarah A Long
*Assistant Examiner* — Raihan R Khandker
(74) *Attorney, Agent, or Firm* — HAUPTMAN HAM, LLP

(57) ABSTRACT

An artificial chordae tendineae implantation system, including a clamping device, puncture device, a pushing device, and a clamp assistance device. The pushing device includes a pushing catheter. The puncture device and the clamping device respectively are movably insertedly mounted within the pushing catheter. An artificial chordae tendineae is accommodated in the clamping device. The clamp assistance device includes a clamp assistance arm movably insertedly mounted within the pushing catheter and a clamp assistance member provided at the distal end of the clamp assistance arm. The clamp assistant member is made of a flexible and/or soft material. The clamp assistance member and the clamp assistance arm are accommodated together in the pushing catheter. The clamp assistance arm pushes the clamp assistance member to pass out from the distal end of the pushing catheter or the distal end of the clamping device.

16 Claims, 19 Drawing Sheets

(56) References Cited

U.S. PATENT DOCUMENTS

| | | | |
|---|---|---|---|
| 2008/0228223 A1* | 9/2008 | Alkhatib | A61B 17/0401 |
| | | | 606/221 |
| 2009/0105729 A1 | 4/2009 | Zentgraf | |
| 2015/0313620 A1* | 11/2015 | Suri | A61B 17/0686 |
| | | | 606/205 |
| 2016/0113769 A1 | 4/2016 | Aklog et al. | |
| 2020/0085577 A1* | 3/2020 | Vola | A61F 2/2457 |

FOREIGN PATENT DOCUMENTS

| | | |
|---|---|---|
| CN | 104244841 A | 12/2014 |
| CN | 107569301 A | 1/2018 |
| CN | 108186163 A | 6/2018 |
| DE | 102011054176 B4 | 2/2016 |
| ES | 2610992 T3 | 5/2017 |
| WO | 0060995 A2 | 10/2000 |
| WO | 0128432 A1 | 4/2001 |
| WO | 2008112237 A2 | 9/2008 |
| WO | 2009133715 A1 | 11/2009 |

OTHER PUBLICATIONS

International Search Report pertaining to PCT/CN2018/100654, filed Aug. 15, 2018, 10 pages.

\* cited by examiner

1

ARTIFICIAL CHORDAE TENDINEAE IMPLANTATION SYSTEM AND CLAMP AIDING APPARATUS THEREOF

CROSS-REFERENCE TO RELATED APPLICATIONS

This application is the National Stage filing under 35 U.S.C. 371 of International Application No. PCT/CN2018/100654, filed on Aug. 15, 2018, which claims the priority and benefit of Chinese Application CN 201710708970.0, filed on Aug. 17, 2017, the contents of which are all hereby incorporated by reference herein in their entirety.

TECHNICAL FIELD

The present disclosure relates to the technical field of medical devices, and relates to a device for repairing heart valve defects, in particular to an artificial chordae tendineae implantation system having a clamping assistance device.

BACKGROUND

The mitral valve is a one-way "valve" between the left atrium (LA) and the left ventricle (LV), which ensures that blood flows from the left atrium to the left ventricle. Referring to FIG. 1, a normal healthy mitral valve has multiple chordae tendineae. The leaflets of the mitral valve are divided into an anterior leaflet and a posterior leaflet. When the left ventricle is in a diastolic state, the anterior leaflet and the posterior leaflet are in an open state, and the blood flows from the left atrium to the left ventricle; when the left ventricle is in a contracted state, the chordae tendineae are stretched to ensure that the leaflets will not be rushed into the atrium by the blood flow, and the anterior leaflet and the posterior leaflet are well closed, thereby ensuring that the blood flows from the left ventricle through the aortic valve (AV) to the aorta. If there is a lesion in the chordae tendineae or papillary muscles, such as a rupture of the chordae tendineae of the posterior leaflet as shown in FIG. 2, when the left ventricle is in a contracted state, the mitral valve cannot return to a closed state as normal, and the impulse of the blood flow will further cause the leaflet to be detached into the left atrium, causing blood reflux.

Chordae tendineae having a lesion or a rupture cannot self-repair. Even if only a few chordae tendineae are ruptured, this could make the tensions of other chordae tendineae increase and cause new ruptures of chordae tendineae. Typical manifestations of a rupture of the chordae tendineae of the mitral valve are acute severe gasping, dyspnea and other left heart failure, and pulmonary edema, partially progressive chronic heart failure. At present, lesions in the chordae tendineae are generally treated by artificial chordae tendineae implantation. This requires adopting invasive open thoracotomy approaches, under general anesthesia, and moderate hypothermic cardiopulmonary bypass as auxiliary support. Such surgical operations have the disadvantages of complicated surgical procedures, high costs, severe trauma, high risks of complications, long hospitalization, and painful recovery processes.

At present, there is a device that implants artificial chordae tendineae by minimally invasive approaches. The device uses a clamping assembly to capture a leaflet, during the process of capturing the leaflet, because the leaflet has been remaining in a flapping state, and the surface of the leaflet is smooth, even when the clamping device has captured the leaflet, the leaflet may slip off the clamping device, thereby causing a prolonged surgical time even a surgical failure. Also, after the leaflet is captured, if the clamping position is found to be not reasonable, the operator has to fine adjust the clamping device, at this time the leaflet is very easily to slip off the clamping device, thereby causing a prolonged surgical time and even a surgical failure.

SUMMARY

In response to the disadvantages of the prior art, the present disclosure provides an artificial chordae tendineae implantation system and its clamping assistance device that assists the clamping device in capturing leaflets stably and prevent the leaflet from slipping off the clamping device.

To solve the technical problem, the present disclosure provides the technical solution:

An artificial chordae tendineae implantation system, including a clamping device, a puncture device, and a pushing device; the pushing device includes a pushing shaft, the puncture device and the clamping device are respectively movably insertedly mounted within the pushing shaft. The clamping device accommodates an artificial chordae tendinea. The implantation system further includes at least one clamping assistance device. The clamping assistance device includes a clamping assistance arm movably insertedly mounted within the pushing shaft and a clamping assistance member disposed on a distal end of the clamping assistance arm. The clamping assistance member is made of an elastic and/or flexible material and deformable. The clamping assistance member and the clamping assistance arm are accommodated together in the pushing shaft. The clamping assistance arm pushes the clamping assistance member out of a distal end of the pushing shaft, the clamping assistance member cooperates with the clamping device to clamp a leaflet.

A clamping assistance device mounted on an artificial chordae tendineae implantation system, the clamping assistance device includes a clamping assistance arm and a clamping assistance member disposed at one end of the clamping assistance arm, the clamping assistance member is made of an elastic and/or flexible material and is deformable to support a leaflet.

The artificial chordae tendineae implantation system of the present disclosure has at least following beneficial technical results over the prior art:

The artificial chordae tendineae implantation system of the present disclosure is provided with a clamping assistance device. A clamping assistance arm of the clamping assistance device is movably insertedly mounted within the pushing shaft, the clamping assistance member passes out of a distal end of the pushing shaft or a distal end of the clamping device. After a leaflet is clamped by a distal clamp and a proximal clamp, the distal end of the clamping assistance device may support the lower surface of the leaflet, and lift the leaflet to the atrial side, thereby reducing the amplitude of the movement of the leaflet, cooperating with the clamping device to stabilize the flapping leaflet. Also, after the clamping assistance device supports the lower surface of the leaflet, if the clamping device is found to be not ideal, the clamping device may be fine adjusted. During the fine adjusting process, the supporting function of the clamping assistance device will prevent the leaflet from slipping off the clamping device.

BRIEF DESCRIPTION OF THE DRAWINGS

To illustrate the technical solutions according to the embodiments of the present disclosure or in the prior art more clearly, the accompanying drawings for describing the embodiments or the prior art are introduced briefly in the following. Apparently, the accompanying drawings in the following description are only some embodiments of the present disclosure, and persons of ordinary skill in the art can derive other drawings from the accompanying drawings without creative efforts.

DETAILED DESCRIPTION OF THE EMBODIMENTS

The present disclosure will be described in details in combination with the accompanying drawings and embodiments such that the purpose, technical solution and advantages of the present disclosure will be more apparent. It should be understood that the particular embodiments are described for the purpose of illustrating as opposed to restricting the present disclosure.

In the field of interventional medical device technology, the orientation near the operator is generally defined as a proximal end, and the orientation away from the operator is defined as a distal end.

Figure 11:
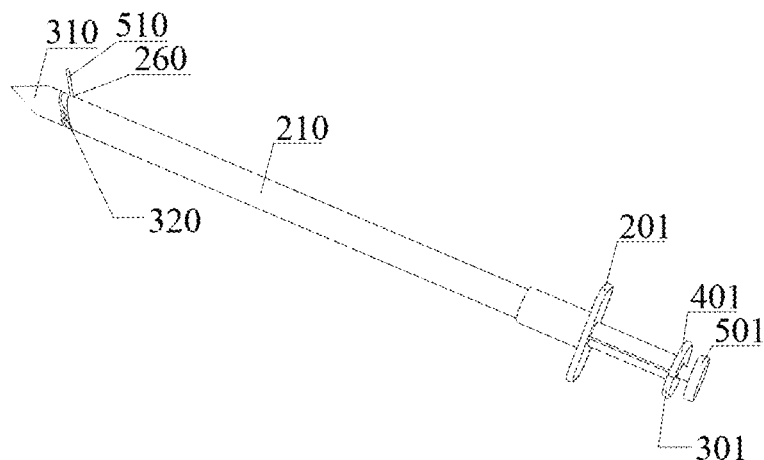
FIG. 11 is a schematic structural view of the artificial chordae tendineae implantation system of the embodiments of the present disclosure.
Figure 12:
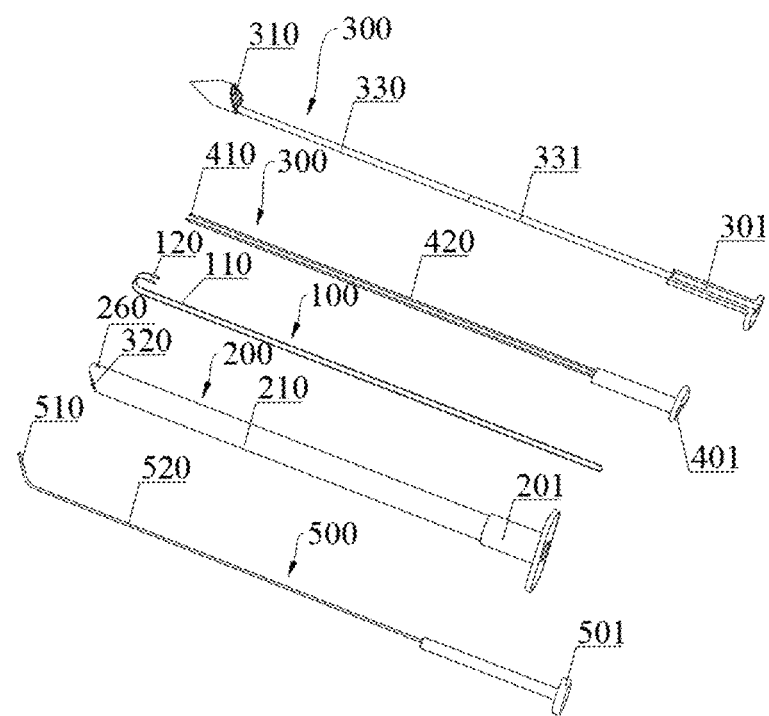
FIG. 12 is an exploded view of the artificial chordae tendineae implantation system of the embodiments of the present disclosure.
Figure 13:
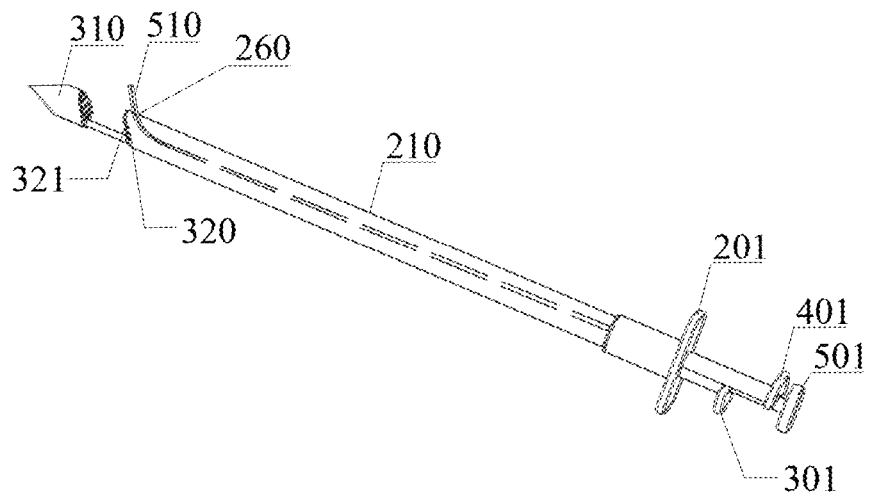
FIG. 13 is a schematic structural view illustrating a separation between the distal clamp and the proximal clamp of the clamping device of the artificial chordae tendineae implantation system of the embodiments of the present disclosure.

Referring to FIG. 3 to FIG. 31, the artificial chordae tendineae implantation system is used to implant artificial chordae tendineae in a patient's body, to replace the natural chordae tendineae having a lesion or a rupture. As shown in FIG. 11 to FIG. 13, the artificial chordae tendineae implantation system includes an artificial chorda tendinea 100, a clamping device 300, a puncture device 400, and a pushing device 200. The pushing device 200 includes a pushing shaft 210. The puncture device 400 and the clamping device 300 are respectively movably insertedly mounted within the pushing shaft 210. The clamping device 300 accommodates the artificial chorda tendinea 100. The puncture device 400 includes two puncture needles 410 and two puncture rods 420 that are respectively connected with the proximal ends of the two puncture needles 410, as shown in FIG. 12. The artificial chordae tendineae implantation system also includes at least a clamping assistance device 500. The clamping assistance device 500 includes a clamping assistance arm 520 that is movably insertedly mounted within the pushing shaft 210, and a clamping assistance member 510 that is disposed at a distal end of the clamping assistance arm 520. The clamping assistance member 510 is used to cooperate with the clamping device 300 to clamp a leaflet. The clamping assistance arm 520 is used to support and push the clamping assistance member 510. The clamping assistance member 510 is made of an elastic and/or flexible material, and the clamping assistance member 510 and the clamping assistance arm 520 are accommodated together in the pushing shaft 210. The clamping assistance arm 520 pushes the clamping assistance member 510 out of the distal end of the pushing shaft 210 or the distal end of the clamping device 300. The clamping assistance member 510 and the clamping device 300 cooperate to clamp the leaflet.

Referring to FIG. 3 to FIG. 6, the artificial chorda tendinea 100 includes a flexible chordae tendinea main body 110. The chordae tendinea main body 110 includes a first end and a second end opposite to the first end. The first end and/or the second end is connected with a fixing member 120. A puncture connecting member 125 used for a non-detachable or detachable connection with the puncture needle 410 is provided on one side of the fixing member 120 facing away from the chordae tendinea main body 110. One end of the chordae tendinea main body 110 is fixed to the leaflet, and the other end is fixed on the ventricular wall or the papillary muscles to replace a diseased chordae tendinea, thereby maintaining the tension between the leaflet and the ventricular wall or the papillary muscles. The flexibility of the chordae tendinea main body 110 means that it can bend freely in the axial direction without stretching. Generally, the chordae tendinea main body 110 is in the form of a flexible wire. The material of the chordae tendinea main body 110 may be a polymer compatible with a human body or a soft metal, particularly a polymer.

Figure 1:
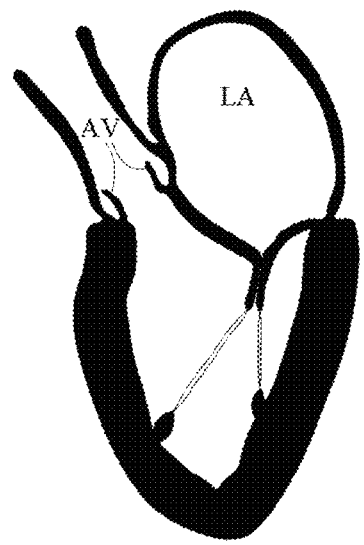
FIG. 1 is a schematic diagram illustrating normal chordae tendineae in a heart.
Figure 2:
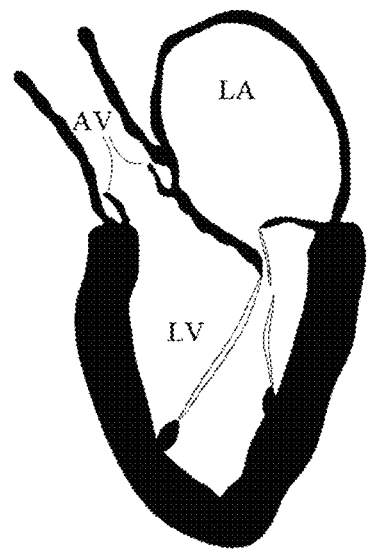
FIG. 2 is a schematic diagram illustrating ruptured chordae tendineae in a heart.
Figure 3:
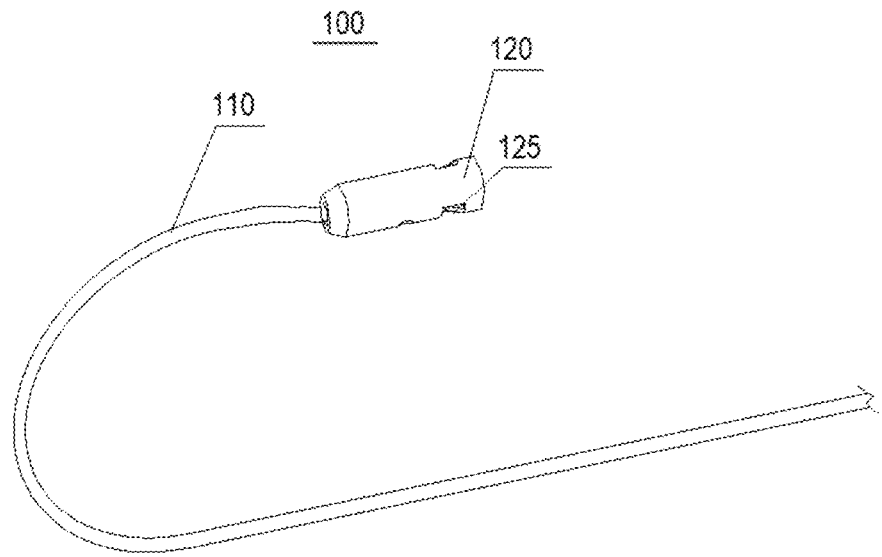
FIG. 3 is a schematic structural view of the artificial chordae tendineae of the artificial chordae tendineae implantation system in accordance with the first implementation manner of the embodiments of the present disclosure.
Figure 4:
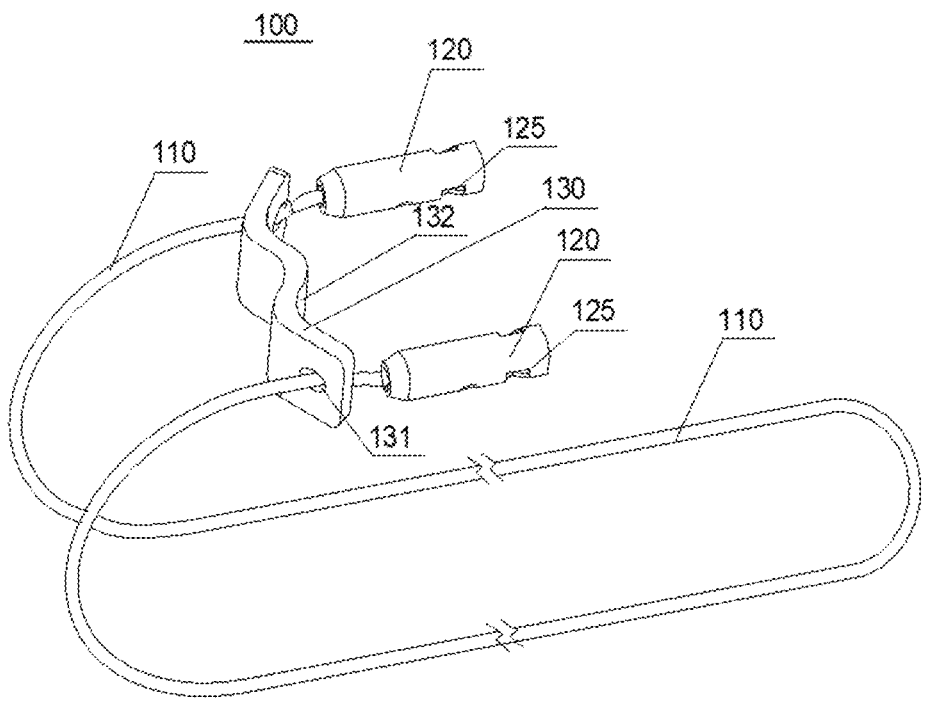
FIG. 4 is a schematic structural view of the artificial chordae tendineae of the artificial chordae tendineae implantation system in accordance with the second implementation manner of the embodiments of the present disclosure.
Figure 5:
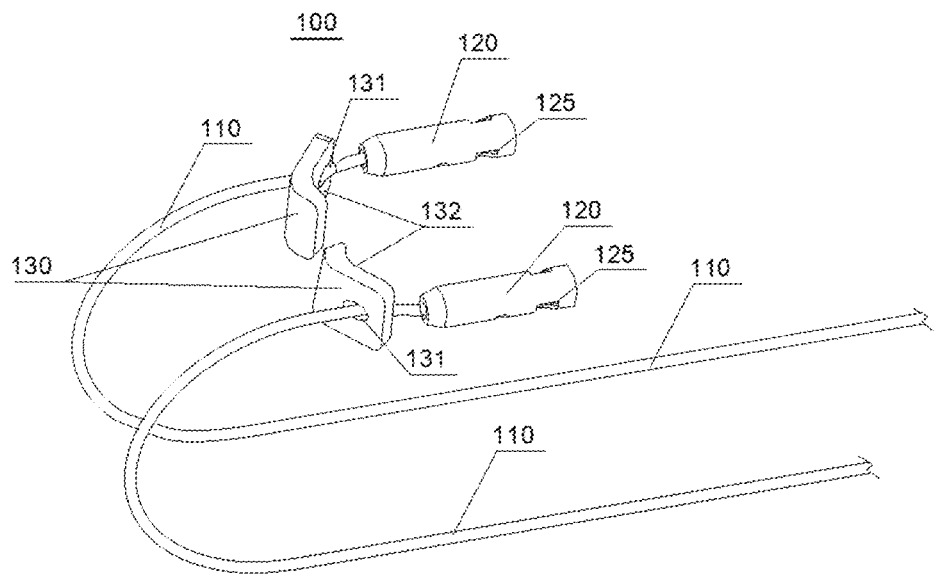
FIG. 5 is a schematic structural view of the artificial chordae tendineae of the artificial chordae tendineae implantation system in accordance with the third implementation manner of the embodiments of the present disclosure.
Figure 6:
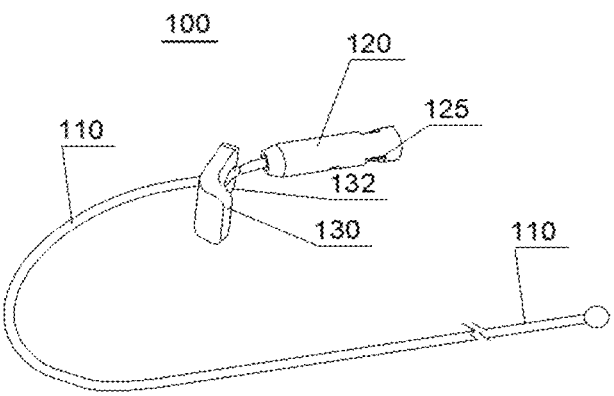
FIG. 6 is a schematic structural view of the artificial chordae tendineae of the artificial chordae tendineae implantation system in accordance with the fourth implementation manner of the embodiments of the present disclosure.

The first end and the second end of the chordae tendinea main body 110 have no difference in direction, importance, and the like. As shown in FIG. 3, the fixing member 120 may be disposed on one end of the chordae tendinea main body 110; as shown in FIG. 4, the fixing member 120 may be disposed on both ends of the chordae tendinea main body 110. As shown in FIG. 5, the number of the artificial chordae tendinea 100 may be one, and could be two or more. In this embodiment, particularly the number of the artificial chordae tendinea 100 is one, and the first end and the second end of the chordae tendinea main body 110 are both provided with a fixing member 120. The chordae tendinea main body 110 is connected with the fixing member 120 in a fixed connection. The fixed connection may be performed by various fastening methods such as tying, winding, welding, bonding, and snap fitting, and the present disclosure is not limiting. For example, one end of the chordae tendinea main body 110 may pass through the fixing member 120 and then is tied to form a larger diameter coil, or the end may be welded to form a larger diameter ball, or the end may be provided with a positioning rod. As shown in FIG. 6, when the fixing member 120 is disposed on the first end of the chordae tendinea main body 110, because the second end of the chordae tendinea main body 110 is not provided with the fixing member 120, the second end is supposed to, by way of tying, winding, or providing a spherical end, a disc-shaped end, or the like, have a diameter of the second end greater than a diameter of the chordae tendinea main body 110, thereby fixing the second end of the chordae tendinea main body 110 on the upper surface of the leaflet.

The fixing member 120 is used to form a detachable or non-detachable connection with the puncture needle 410, and a shape of the fixing member 120 corresponds to different connecting manners. The fixing member 120 is provided with a puncture connecting member 125 for connecting with the puncture needle 410. Because the distal end of the puncture needle 410 is generally in a shape of a sharp cone, a contact area between the fixing member 120 and the outer surface of the puncture needle 410 should be as large as possible, to form a stable connection. As such, an accommodation chamber 121 for accommodating the puncture needle is disposed on one side of the fixing member 120 facing away from the chordae tendinea main body 110, and the puncture connecting member 125 is disposed in the accommodation chamber 121. A shape of the accommodation chamber 121 corresponds to a shape of the distal end of the puncture needle 410. The shape of the accommodation chamber 121 is generally conical or cylindrical. The fixing member 120 is generally cylindrical, and the shape of the cross section may be various shapes such as a circle, an ellipse, a polygon, and the like, and generally particularly a circular shape and an elliptical shape. The puncture needle 410 is provided with a chordae tendinea connecting member 411 that forms a fixed connection with the puncture connecting member 125 of the artificial chordae tendinea 100. The chordae tendinea connecting member 411 cooperates with the puncture connecting member 125 to improve the stability of the connection between the puncture needle 410 and the artificial chordae tendinea 100.

There are various connecting manners between the puncture connecting member 125 of the fixing member 120 and the chordae tendinea connecting member 411 of the puncture needle 410.

Figure 7:
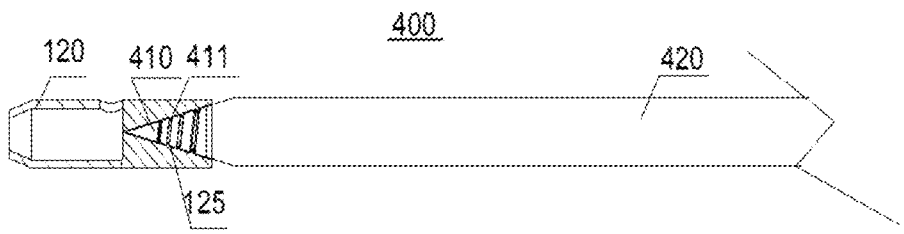
FIG. 7 to FIG. 10 are schematic structural views of the connection between a fixing member and a puncture needle of the artificial chordae tendineae implantation system in accordance with various implementation manners of the embodiments of the present disclosure.

Referring to FIG. 7, in accordance with the first implementation manner, the puncture connecting member 125 is an internal thread disposed on the side wall of the accommodation chamber 121. The chordae tendinea connecting member 411 is an external thread disposed on the outer surface of the puncture needle 410; after the puncturing is performed, the puncture needle 410 is in a threaded connection with the fixing member 120 of the artificial chordae tendinea 100 to form a detachable connection.

Figure 8:
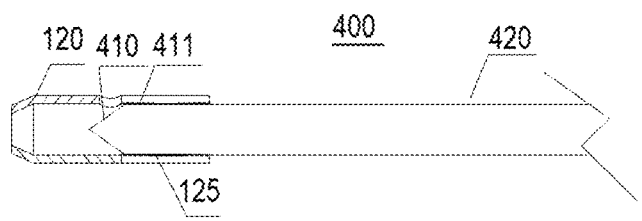

Referring to FIG. 8, in accordance with the second implementation manner, the puncture connecting member 125 is an adhesive layer disposed on the side wall of the accommodation chamber 121. The chordae tendinea connecting member 411 is an adhesive layer disposed on the outer surface of the puncture needle 410. Specifically, an adhesive is applied to the outer surface of the puncture needle 410 and the inner wall of the accommodation chamber 121 in whole or partially to form an adhesive layer. After the puncturing is performed, the adhesive layer of the puncture connecting member 125 of the fixing member 120 is adhesively fixed to form a non-detachable whole.

Figure 9:
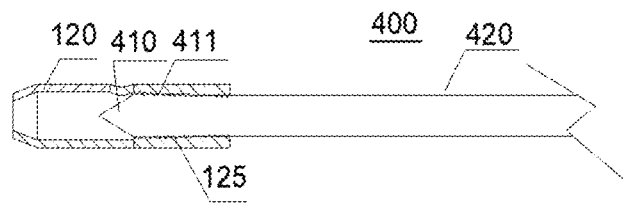

Referring to FIG. 9, in accordance with the third implementation manner, the puncture connecting member 125 is a rough surface provided on the side wall of the accommodation chamber 121. The chordae tendinea connecting member 411 is a rough surface provided on the outer surface of the puncture needle 410. After the puncturing is performed, the fixing member 120 and the puncture needle by way of the frictional resistance form a detachable connection.

Figure 10:
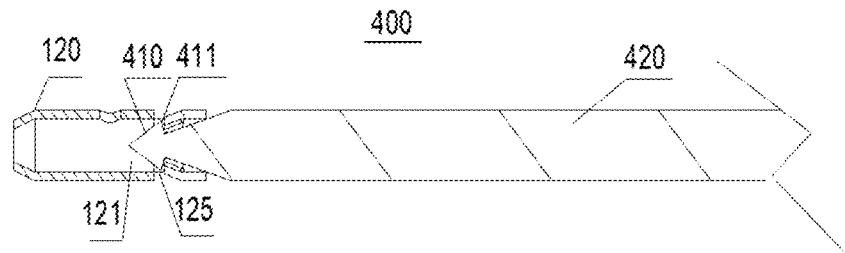

Referring to FIG. 10, in accordance with the fourth implementation manner, the puncture connecting member 125 is at least one indentation or a hole disposed on the side wall of the accommodation chamber 121. The chordae tendinea connecting member 411 is at least one protrusion or at least a circle of protruding edge that is disposed at the distal end of the puncture needle 410 and forms an interference fit, a snap fit connection or a key connection with the puncture connecting member 125 of the fixing member 120. The hole or indentation may be a blind hole or a through hole, as long as a shape of the hole or indentation substantially corresponds to a protrusion or protruding edge disposed on the puncture needle, so as to form a snap fit connection. In this embodiment, particularly three indentations are disposed to improve the stability of the connection between the fixing member 120 and the puncture needle 410, and to reduce the amplitude of the shaking of the puncture needle 410 after the connection.

The key connection can be selected from key connection manners such as a flat key connection, a spline connection, and the like, and forms a tight key connection, such that a pulling force can also be transmitted in the axial direction. The key connection structure is a conventional technique, and details are not described herein again.

Referring to FIG. 4 to FIG. 6, in order to increase the contact area between the artificial chordae tendinea 100 and the leaflet, so as to efficiently reduce the risk of tearing the leaflet by the artificial chordae tendinea 100, particularly an anti-slip member 130 is sleeved on the chordae tendinea main body 110, and the anti-slip member may slide along the axial direction of the chordae tendinea main body 110. As such, when the puncture needle 410 punctures the leaflet and is connected to the fixing member 120 of the artificial chordae tendinea 100, the anti-slip member 130 is disposed in advance on the artificial chordae tendinea 100, the anti-slip member 130 may be pushed to the puncture point, and the anti-slip member 130 and the artificial chordae tendinea 100 may be fixed together on the leaflet.

The specific configuration manner of disposing the anti-slip member 130 on the artificial chordae tendinea 100 is: a through hole 131 is disposed on the anti-slip member 130, and the chordae tendinea main body 110 passes through from the through hole 131. The number of the provided through holes 131 is related to the fixing form of the anti-slip member 130.

In accordance with one implementation manner, each chordae tendinea main body 110 is provided with an anti-slip member 130. In this structure, the anti-slip member 130 is provided with a through hole 131, and the chordae tendinea main body 110 passes through the through hole 131 (as shown in FIG. 5 and FIG. 6).

In accordance with another implementation manner, each chordae tendinea main body 110 is provided with at least two anti-slip members 130. In this structure, the anti-slip member 130 is provided with at least two through holes 131, and the first end and the second end of the chordae tendinea main body 110 pass through different through holes 131 respectively (as shown in FIG. 4).

In accordance with still another implementation manner, a plurality of chordae tendinea main bodies 110 share a common anti-slip member 130. In this structure, the anti-slip member 130 is provided with at least two through holes 131, and at least two chordae tendinea main bodies 110 pass through different through holes 131 respectively.

In order to prevent the anti-slip member 130 from slipping off the chordae tendinea main body 110, the cross-sectional diameter of the through hole 131 of the anti-slip member 130 is smaller than the cross-sectional diameter of the fixing member 120. And the free end of the chordae tendinea main body 110 that is not provided with a fixing member 120 should, by way of tying, or providing a spherical end, a disc-shaped end, or the like, have a diameter of the free end larger than the diameter of the through hole 131 of the anti-slip member 130 (as shown in FIG. 6).

Referring to FIG. 4 to FIG. 6, in order to disperse the force on the leaflet by the chordae tendinea main body 110 to the contact area between the anti-slip member 130 and the leaflet as much as possible, the anti-slip member 130 needs to fit the leaflet as much as possible. As such, the anti-slip member 130 is provided with a fitting surface 132 that fits the leaflet. Except for the fitting surface 132, the detailed structure of the anti-slip member 130 has no restriction, and may have various structures: for example it may be in the form of a sheet shape, a disc-shape, or a spherical shape having a certain area, or even an irregular shape, particularly a sheet shape. The structure of the anti-slip member 130 may be a non-porous structure, a mesh structure, a bar-shape structure, or the like. The anti-slip member 130 should be made of an elastic material or a non-elastic biocompatible material. Specifically, the anti-slip member 130 is selected from at least one of an elastic spacer, a patch, a pledge, a mesh structure, a disc-shape structure, or a double disc-shape structure. The anti-slip member 130 having a disc-shape structure or a double disc-shape structure is similar to the occluder in the prior art, and will not be described herein. Particularly, in order to reduce the overall size of the devices, an anti-slip member 130 having a disc-shape structure or a double disc-shape structure should be made of a shape memory material.

With further reference to FIG. 11 to FIG. 13, the pushing shaft 210 is a tubular body having a certain axial length or a rod having at least one lumen. The pushing shaft 210 is provided with a plurality of mutually separated lumens in the axial direction. The pushing shaft 210 may be an integrally formed multi-lumen tube, or the outer tube and the inner tube may be sleeved and secured together to form the pushing shaft 210 in an integral structure. The pushing shaft 210 may be made of a biocompatible polymer (for example, polyoxymethylene POM, polyethylene PE, nylon PA, polyvinyl chloride PVC, acrylonitrile-butadiene-styrene copolymer ABS, thermoplastic elastomer Pebax or Polyurethane PU), or a metal (for example, stainless steel or nickel-titanium alloy). The proximal end of the pushing shaft 210 is provided with the first handle 201 for operating the pushing shaft 210 to push towards the distal end or retract towards the proximal end.

The puncture device 400 is insertedly mounted within an lumen of the pushing shaft 210. The puncture needle 410 is used to puncture the leaflet and to be connected to the fixing member 120 of the artificial chordae tendinea 100, so as to pull the chordae tendinea main body 110 towards the proximal end. For the purpose of facilitating the puncturing and reducing the diameter of the puncture point formed on the leaflet, particularly the distal end of the puncture needle 410 is a conical straight tip. The conical straight tip in comparison with a hook-shape needle in the prior art, forms a smaller puncture point on the leaflet, easier to recover after the surgery. The artificial chordae tendineae implantation system of this embodiment forms a puncture point on the leaflet that generally has a diameter ranging from 0.3 mm to 1.5 mm. Further, by selecting a suitable shape and diameter of the puncture needle 410, the diameter of the puncture point can be limited to about 0.7 mm.

The proximal end of the puncture rod 420 is provided with the third handle 401. The puncture rod 420 is movably insertedly mounted within the lumen of the pushing shaft 210. The proximal end of the third handle 401 passes through from the proximal end of the pushing shaft 210. As such, by way of operating the axial movement of the third handle 401, the puncture rod 420 is driven to move along the axial direction of the pushing shaft 210, to further drive the puncture needle 410 to puncture towards the distal end or to retract towards the proximal end. After the leaflet is clamped, the puncture needle 410 is driven by the third handle 401 to penetrate the leaflet and is connected with the fixing member 120 of the artificial chordae tendinea 100, then the puncture needle 410 and the artificial chordae tendinea 100 are connected by the fixing member 120 as a whole.

The clamping device 300 includes a clamping push rod 330, a distal clamp 310, and a proximal clamp 320. The clamping push rod 330 is insertedly mounted within an lumen of the pushing shaft 210. The proximal clamp 320 is disposed at the distal end of the pushing shaft 210. The distal clamp 310 is disposed at the distal end of the clamping push rod 330. A clamping surface 321 is disposed at the distal end of the proximal clamp 320. A clamping surface 311 is disposed at the proximal end of the distal clamp 310. The proximal end of the clamping push rod 330 passes through out of the proximal end of the pushing shaft 210 and is provided with the second handle 301. As shown in FIG. 13, as such, the second handle 301 is driven towards the distal end, to drive the clamping push rod 330 to move towards the distal end, making the distal clamp 310 move away from the proximal clamp 320, and the clamping device 300 remains in an open state. At this time the distal end of the artificial chordae tendineae implantation system may be fine adjusted, after the leaflet enters into a leaflet accommodation space formed between the distal clamp 310 and the proximal clamp 320, the second handle 301 is retracted towards the proximal end, to drive the clamping push rod 330 to move towards the proximal end, making the distal clamp 310 move closer to the proximal clamp 320, and the clamping device 300 is in a closed state, as shown in FIG. 11. At this time, the leaflet is clamped and secured by the clamping device 300. The shapes of the proximal clamp 320 and the distal clamp 310 should conform to the shape of the pushing shaft 210, to form a smooth overall body, facilitating the pushing and reducing damages to the patients' wounds. It is understood that, the state of driving the second handle 301 towards the distal end to make the distal clamp 310 move away from the proximal clamp 320, may also be achieved by retracting the first handle 201 and the pushing shaft 210 towards the proximal end.

Referring to FIG. 11 to FIG. 15, to improve the stability of the clamping, the clamping surface 321 of the proximal clamp 320 should mutually fit the clamping surface 311 of the distal clamp 310, and separately have relatively large leaflet contact areas. Particularly, both clamping surfaces 311, 321 are disposed obliquely, i.e., the clamping surfaces 311, 321 and the axial direction of the pushing shaft 210 have an angle of less than 90°. In addition, at least one of the clamping surfaces 311, 321 is provided with a clamping reinforcement member 312 for enhancing the clamping force. Particularly, the clamping reinforcement member is at least one of a protrusion, a rib, an indentation, and a recess provided on the clamping surface. In this embodiment, the clamping surface 311 of the distal clamp 310 is provided with ribs as the clamping reinforcement member 312, and the ribs are parallel. The clamping surface 311 is stepped.

Figure 14:
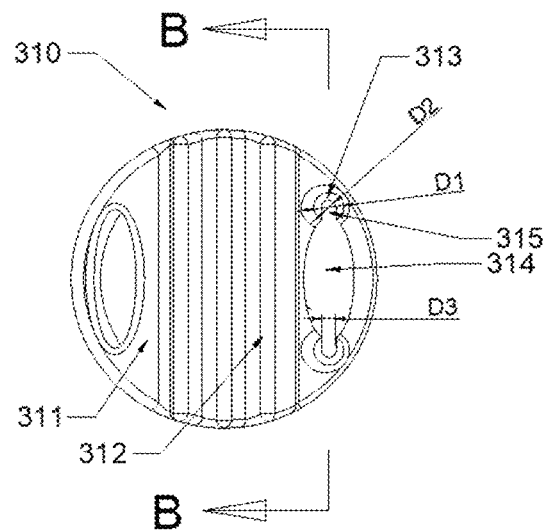
FIG. 14 is a schematic structural view of a clamping surface of the distal clamp of the clamping device of the artificial chordae tendineae implantation system of the embodiments of the present disclosure.
Figure 15:
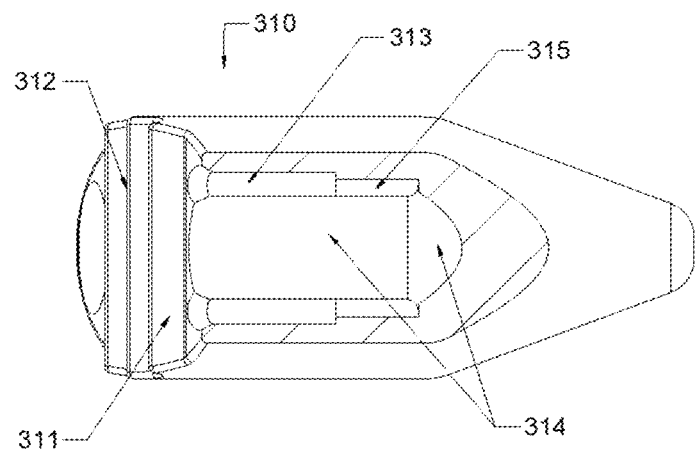
FIG. 15 is a cross-sectional view along the line B-B of FIG. 14.

Referring to FIG. 14 to FIG. 15, an artificial chordae tendinea channel 331 is disposed in the axial direction within the clamping push rod 330, and an artificial chordae tendinea accommodation chamber 315 is disposed in the distal clamp 310. The artificial chordae tendinea accommodation chamber 315 is connected with the artificial chordae tendinea channel 331. The chordae tendinea main body 110 of the artificial chordae tendinea 100 is accommodated in the artificial chordae tendinea channel 331 and the artificial chordae tendinea accommodation chamber 315.

The clamping surface 311 of the distal clamp 310 is provided with an accommodation indentation 314 for accommodating the anti-slip member 130. The accommodation indentation 314 is radially connected with the artificial chordae tendinea accommodation chamber 315.

The clamping surface 311 of the distal clamp 310 is also provided with a fixing chamber 313 for accommodating the fixing member 120 of the artificial chordae tendinea 100. The fixing chamber 313 is axially connected with the artificial chordae tendinea accommodation chamber 315. The fixing chamber 313 is radially connected with the accommodation indentation 314. As such, the fixing member 120 of the artificial chordae tendinea 100 is accommodated in the distal clamp 310, and the proximal end of the fixing member 120 corresponds to the puncture needle 410. After the puncture needle 410 is connected with the fixing member 120, by retracting the puncture rod 420 towards the proximal end, the puncture needle 410, the fixing member 120, the chordae tendinea main body 110 and the anti-slip member 130 are driven to be simultaneously pulled out from the clamping surface 311 of the distal clamp 310, till the puncture needle 410, the fixing member 120, and the chordae tendinea main body 110 jointly pass through the leaflet, and the anti-slip member 130 fits the upper surface of the leaflet.

The fixing chamber 313 is axially connected with the artificial chordae tendinea accommodation chamber 315. The fixing chamber 313 is used to fix the fixing member 120 of the artificial chordae tendinea 100 inside the fixing chamber 313, and pull the fixing member 120 after pulled by external forces from the fixing chamber 313 smoothly. As such, the shape of the fixing chamber 313 corresponds to the shape of the fixing member 120, and a diameter of an inscribed circle of the fixing chamber 313 is larger than a diameter of a circumcircle of the artificial chordae tendinea accommodation chamber 315. Particularly, a ratio of the diameter of the circumcircle of the artificial chordae tendinea accommodation chamber 315 to the diameter of the inscribed circle of the fixing chamber 313 is (0.2-0.4): 1. When the cross sections of the fixing chamber 313 and the artificial chordae tendinea accommodation chamber 315 are both circular, the diameter of the inscribed circle of the fixing chamber 313 is the diameter of the circular cross section of the fixing chamber 313, the diameter of the circumcircle of the artificial chordae tendinea accommodation chamber 315 is the diameter of the circular cross section of the artificial chordae tendinea accommodation chamber 315. In this embodiment, the cross section of the fixing chamber 313 is circular with a diameter D1, and the cross section of the artificial chordae tendinea accommodation chamber 315 is circular with a diameter D2, and D2 is 30% of D1. The purpose of this configuration is: if D2 is too large, when the puncture needle 410, driven by the puncture rod 420, is engaged with the fixing member 120 of the artificial chordae tendinea 100, due to the pushing force towards the distal end by the puncture rod 420, the fixing member 120 may slip from the fixing chamber 313 into the artificial chordae tendineae accommodation chamber 315, and consequently the connection between the puncture needle 410 and the fixing member 120 of the artificial chordae tendinea 100 cannot be achieved in a one-time success, thereby prolonging the surgical time; if D2 is too small, the chordae tendinea main body 110 of the artificial chordae tendinea 100 cannot pass smoothly through the artificial chordae tendineae accommodation chamber 315, and consequently, after the puncture needle 410 is connected with the fixing member 120 of the artificial chordae tendinea 100, the artificial chordae tendinea 100 cannot be smoothly pulled out of the clamping surface 311 of the clamping push rod 330.

In order to smoothly pull both the chordae tendinea main body 110 and the anti-slip member 130 out of the clamping surface 311 of the distal clamp 310, the fixing chamber 313 is radially connected with the accommodation indentation 314. Particularly, a width D3 of the connected portion between the fixing chamber 313 and the accommodation indentation 314 is 20%-50% of D1. The purpose of this configuration is: if D3 is too large, the fixing member 120 of the artificial chordae tendinea 100 cannot be firmly secured in the fixing chamber 313 of the distal clamp 310, and is easy to slip from the fixing chamber 313, causing malfunctioning of the artificial chordae tendineae implantation system; if D3 is too small, after the puncture needle 410 is connected with the fixing member 120 of the artificial chordae tendinea 100, the fixing member 120 cannot be smoothly pulled out of the fixing chamber 313, causing a surgical failure. It is understood that, in other embodiments, the cross sections of the fixing chamber 313 and the artificial chordae tendinea accommodation chamber 315 can also be elliptical, triangular, quadrilateral, polygonal, and the like, as long as the shape of the fixing chamber 313 mutually fits the shape of the fixing member 120 and the shape of the artificial chordae tendineae accommodation chamber 315 does not affect the smooth passing through of the chordae tendinea main body 110 within the artificial chordae tendineae accommodation chamber 315.

The prior art techniques expose the artificial chordae tendineae to outside the devices, causing the outer surface of the devices to be not smooth, thereby causing the devices upon entering the human body to increase the frictional damage to the tissues and at the same time the problem of blood leakage, increasing the risk of postoperative complications. The fixing chamber 313 disposed in the distal clamp 310 facilitates disposing and securing the artificial chordae tendinea 100 inside the artificial chordae tendineae implantation system, thereby preventing the frictional damage to the tissues during the entry of the artificial chordae tendineae into the human body.

Further: the fixing chamber 313 of the distal clamp 310 may secure the fixing member 120 of the artificial chordae tendinea 100 and the anti-slip member 130, without loosening the distal clamp 310 and the proximal clamp 320, and can pull the chordae tendinea main body 110 and the anti-slip member 130 to the leaflet, such that when the clamping device 300 changes from a closed state to an open state, at the moment when the leaflet is detached from the clamping device 300 and resumes flapping, the chordae tendinea main body 110 will not contact the leaflet alone, thereby avoiding the linear cutting of the chordae tendinea main body 110 on the flapping leaflet.

In the prior art, the artificial chordae tendineae are implanted with a U-shaped loop combined with a hook-shaped needle, thereby causing the edge of the leaflet to be folded and form an artificial gap, which will not form a matching edge, making it easy to result in the mitral regurgitation and a non-ideal surgical result. According to the artificial chordae tendineae implantation system of the present disclosure, because the chordae tendinea main body 110 is accommodated in the clamping push rod 330, and the distance from the fixing chamber 313 of the distal clamp 320 to the edge of the distal clamp 320 is the distance between the implanted artificial chordae tendinea 100 and the leaflet edge, the spacing between each artificial chordae tendinea 100 and the edge of the leaflet is substantially the same, thereby effectively preventing the edge of the leaflet from folding and enhancing the surgical effect.

Figure 16:
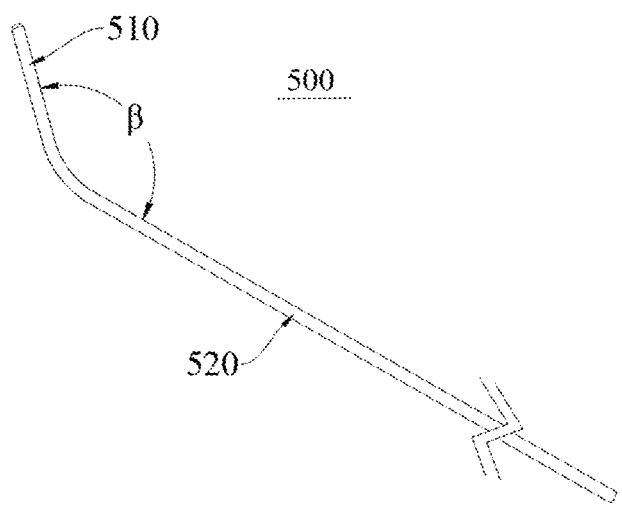
FIG. 16 is a schematic structural view of the clamping assistance device of the artificial chordae tendineae implantation system in accordance with the first implementation manner of the embodiments of the present disclosure.

As shown in FIG. 16, for facilitating the pushing, the fourth handle 501 is disposed at the proximal end of the clamping assistance arm 520.

Figure 18:
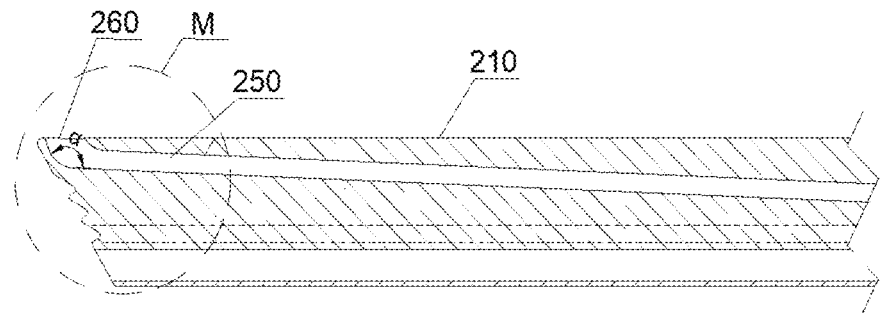
FIG. 18 is a schematic structural view of the pushing shaft of the pushing device of the artificial chordae tendineae implantation system in accordance with the first implementation manner of the embodiments of the present disclosure.
Figure 19:
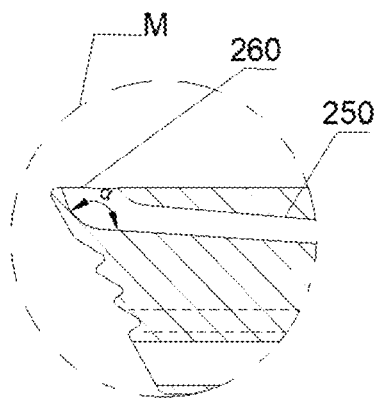
FIG. 19 is a partially enlarged view of M in FIG. 18.

As shown in FIG. 12 and FIG. 18 to FIG. 19, an assistance arm accommodation chamber 250 is disposed in the pushing shaft 210 along the axial direction, for accommodating the clamping assistance member 510 and the clamping assistance arm 520.

Figure 20:
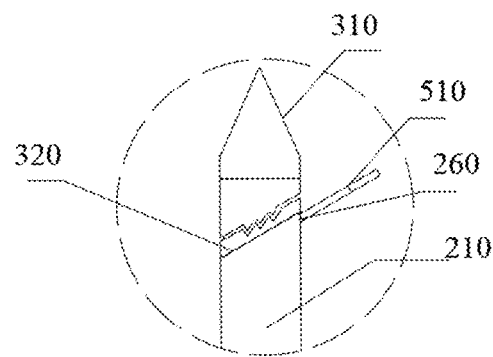
FIG. 20 is a schematic structural view of the distal end of the artificial chordae tendineae implantation system of the embodiments of the present disclosure.

As shown in FIG. 18 to FIG. 20, the side wall of the pushing shaft 210 is provided with an opening 260. The opening 260 is through connected with the assistance arm accommodation chamber 250. When the fourth handle 501 is driven towards the distal end, the clamping assistance arm 520 can be driven to push the clamping assistance member 510 to pass out of the opening 260. The opening 260 can also be disposed on the clamping surface 321 of the proximal clamp 320 or the sidewall of the proximal clamp 320 and in through connection with the assistance arm accommodation chamber 250.

Figure 22:
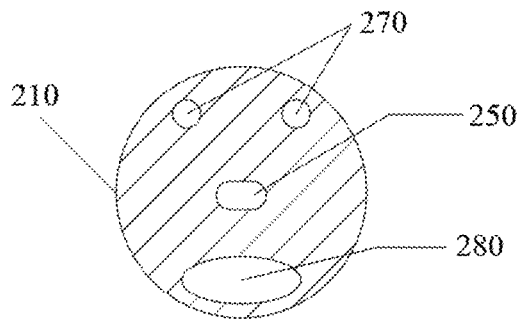
FIG. 22 is a radial sectional view of the pushing shaft of the pushing device of the artificial chordae tendineae implantation system in accordance with the embodiments of the present disclosure.

Referring to FIG. 22, the clamping push rod 330 is insertedly mounted within the lumen 280 of the pushing shaft 210. Two puncture rods 420 are insertedly mounted within the two lumens 270 of the pushing shaft 210, and the axis of the clamping push rod 330 and the axis of the puncture rod 420 are both parallel with the axis of the pushing shaft 210. The clamping push rod 330 is disposed on one side of the pushing shaft 210, and the puncture rod 420 is disposed on the other side of the pushing shaft 210. In order to reduce the patient's injury and incision, the overall outer diameter of the pushing shaft 210 should be minimized, particularly the assistance arm accommodation chamber 250 is disposed between the accommodation chamber 280 of the clamping push rod 330 and the accommodation chamber 270 of the puncture rod 420.

Referring to FIG. 11 to FIG. 12 and FIG. 22, during the puncturing, the clamping push rod 330 contacts the edge of the leaflet, the distal clamp 310 and the proximal clamp 320 can only clamp part of the leaflet, at this time in order to stabilize the flapping leaflet to facilitate the puncturing, a supporting force is applied to somewhere away from the edge of the leaflet, so that it is necessary to have a certain angle between the clamping assistance member 510 and the pushing shaft 210, thereby making the clamping assistance member 510 support the lower surface at somewhere away from the edge of the leaflet. As such, it is desirable to form an angle ranging 120°-150° between the axis of the distal end of the assistance arm accommodation chamber 250 and the axis of the pushing shaft 210. The assistance arm accommodation chamber 250 is disposed along the axial direction of the pushing shaft 210, and may be parallel or non-parallel to the central axis of the pushing shaft 210, specifically corresponding to the structure of the clamping assistance device 500.

Referring to FIG. 18 and FIG. 19, in accordance with the first implementation manner of the pushing shaft 210, the assistance arm accommodation chamber 250 is disposed along the axial direction of the pushing shaft 210, the assistance arm accommodation chamber 250 is substantially straight, the whole assistance arm accommodation chamber 250 is obliquely disposed in the pushing shaft 210, and an angle α between the axis of the distal end of the assistance arm accommodation chamber 250 and the axis of the pushing shaft 210 ranges from 120° to 150°.

Figure 21:
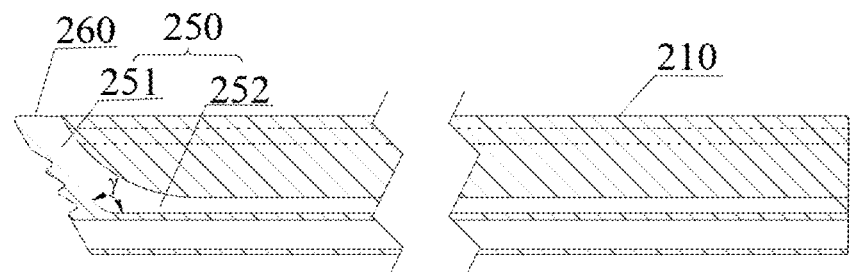
FIG. 21 is a schematic structural view of the pushing shaft of the artificial chordae tendineae implantation system in accordance with the second implementation manner of the embodiments of the present disclosure.

Referring to FIG. 21, in accordance with the second implementation manner of the pushing shaft 210, the assistance arm accommodation chamber 250 includes the distal chamber 251 and the proximal chamber 252. The proximal chamber 252 is substantially parallel to the axis of the pushing shaft 210, an angle γ between the distal chamber 251 and the proximal chamber 252 ranges from 120° to 150°. The distal chamber 251 has a smooth transition to the proximal chamber 252, so as not to affect the smooth passing through of the clamping assistance arm 520 in the assistance arm accommodation chamber 250.

The shape of the assistance arm accommodation chamber 250 corresponds to the shape of the clamping assistance arm 520, and the cross section may be circular or elliptical, crescent, semicircular, polygonal, or the like. Particularly, it is round without corners or elliptical.

Figure 17:
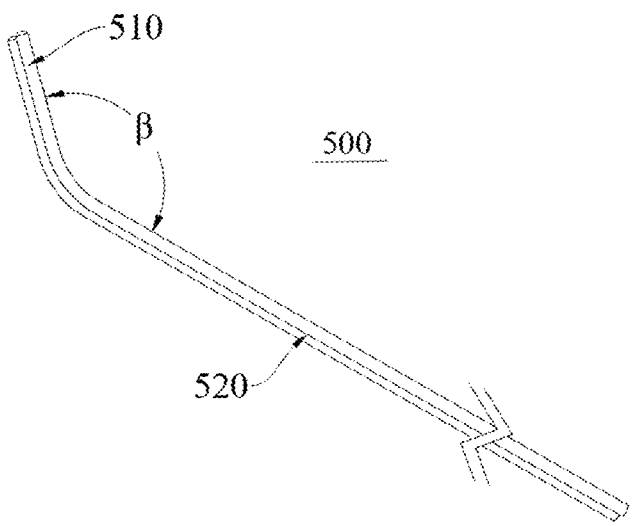
FIG. 17 is a schematic structural view of the clamping assistance device of the artificial chordae tendineae implantation system in accordance with the second implementation manner of the embodiments of the present disclosure.

Referring to FIG. 16 and FIG. 17, an angle β between the axis of the clamping assistance member 510 of the clamping assistance device 500 and the axis of the clamping assistance arm 520 ranges 120°-150°. The clamping assistance member 510 is used for assisting the clamping device 300 in clamping the leaflet. The clamping assistance member 510 is made of elastic and/or flexible materials, to accommodate the anatomical structure of the leaflet and the amplitude of movement of the leaflet, and to effectively avoid damages to the leaflet. For example, a metal, a polymer or a metal-polymer composite material can be selected. The elastic material is particularly a shape memory material.

Referring to FIG. 16 to FIG. 17, the clamping assistance device 500 is generally L-shaped and is formed by at least one support rod.

As shown in FIG. 16, in accordance with the first implementation manner of the clamping assistance device 500, the clamping assistance member 510 is substantially L-shaped and is formed by a support rod.

As shown in FIG. 17, in accordance with the second implementation manner of the clamping assistance device 500, the clamping assistance member 510 is generally L-shaped and formed by two parallel support rods.

The support rod may be a solid or hollow structure of a single-layer or multi-layer composite structure, or may be wound from a single wire or a plurality of wires. The cross section of the support rod may be a regular circular or elliptical shape, a crescent shape, a semicircular shape, a polygonal shape, or the like, and is particularly a circular shape. The clamping assistance member 510 is particularly made of an elastic material having a shape memory function, such as a shape memory metal. The clamping assistance member 510 is smooth, for example, by laser spot welding to form a smooth round head without defects like burrs, edges, corners and the like.

In order to facilitate the support of the lower surface of the leaflet, the clamping assistance member 510 particularly has a cross-sectional dimension that is greater than the cross-sectional dimension of the clamping assistance arm 520 to establish a stable support for the leaflet.

The support rod of the clamping assistance arm 520 has an axial length, and may be a hollow or solid structure of a single-layer or multi-layer composite structure made of a metal or polymer, or may be wound from a single wire or a plurality of wires. FIG. 16 illustrates that the clamping assistance arm 520 is a single support rod. FIG. 17 illustrates that the clamping assistance arm 520 is two parallel support rods. The section of the clamping assistance arm 520 may be a regular circular or elliptical, crescent, semi-circular, polygonal or ring-shape, particularly circular. The clamping assistance arm 520 is particularly made of a material having a shape memory function and may be made of a metal, a polymer or a metal-polymer composite material. The clamping assistance arm 520 particularly has a certain hardness or stiffness to provide supporting and pushing abilities. The clamping assistance arm 520 is disposed in advance in the assistance arm accommodation chamber 250 of the pushing shaft 210. As shown in FIG. 20, after the clamping assistance member 510 is pushed out from the opening of the assistance arm accommodation chamber 250, the clamping assistance member 510 fits the lower surface of the leaflet, and the clamping assistance member 510 having elasticity or flexibility can well accommodate the amplitude of the movement of the leaflet, without causing penetration or stabbing to the leaflet for being too hard. The hardness of the clamping assistance arm 520 is higher, better for transmitting the pushing force, so as to move the fourth handle 501 to drive the whole clamping assistance arm 520 with respect to the pushing shaft 210 to move towards the distal end or retract towards the proximal end.

In other embodiments, the clamping assistance member 510 and the clamping assistance arm 520 may be integrally formed, or be detachably or non-detachably connected.

The clamping assistance member 510 and the clamping assistance arm 520 are integrally made of a hollow or solid metal rod or a polymer rod having a certain axial length, a single or multi-layer composite structure, or may be wound from a single wire or a plurality of wires.

A non-detachable connection is: the clamping assistance arm 520 and the clamping assistance member 510 are separately processed and then fixedly connected together by welding, bonding or the like.

A detachable connection is: the clamping assistance arm 520 and the clamping assistance member 510 are separately processed and then fixedly connected together by socketing, a threaded connection, an interference fit or the like. The above-mentioned connecting manners are conventional techniques and details are not described herein again.

The supporting of the clamping assistance arm 520 and the flexibility of the clamping assistance member 510 may be achieved by using different materials to make the clamping assistance member 510 and the clamping assistance arm 520 respectively. That is, the clamping assistance arm 520 is a rod-shape or tubular structure made of a hard material; the clamping assistance member 510 may be made of an elastic, flexible material or a combination of both.

Figure 23:
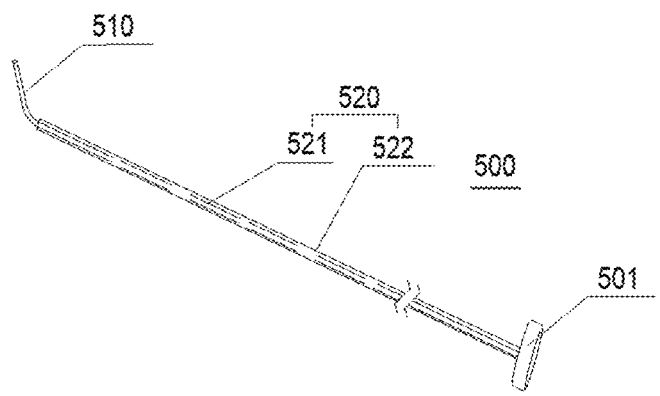
FIG. 23 is a schematic structural view of the clamping assistance device of the artificial chordae tendineae implantation system in accordance with the third implementation manner of the embodiments of the present disclosure.

Referring to FIG. 23, in accordance with the third implementation manner of the clamping assistance device 500, the clamping assistance device 500 is substantially L-shape. The clamping assistance arm 520 includes an assistance arm main body 521 that is elastic or flexible, and a supporting body 522 that is made of a hard material and disposed inside or outside the assistance arm main body 521. The hard supporting body 522 is used to support the assistance arm main body 521. The supporting body 522 can be installed as a set with or disposed in parallel with the assistance arm main body 521. That is, first using flexible material to make the whole rod body or tubular body as the clamping assistance member 510 and the assistance arm main body 521, then having an inner tube with a higher hardness insertedly mounted within the lumen of the assistance arm main body 521, or, having an outer tube with a higher hardness that is used as the supporting body 522 sleeved on part of the outer surface of or disposed in parallel with the assistance arm main body 521 to enhance the supporting of the proximal end of the clamping assistance arm 520; also a heat shrinkable tube may be used as the supporting body 522 to warp around the flexible outer surface of the assistance arm main body 521, then the heat shrinkable tube is heated to shrink and warp around the outer surface of the assistance arm main body 521 to enhance the supporting abilities. It is also understood that, for an assistance arm main body 521 wound from a single wire or a plurality of wires, a thermoplastic elastomer such as Pebax may be wrapped around part of the outer surface of the assistance arm main body 521, and then the thermoplastic elastomer is heated to melt and wrap the outer surface meanwhile infiltrating into the gap between multiple or single wire (i.e., the supporting body 522 is disposed outside and inside the assistance arm main body 521), thereby improving the supporting of the assistance arm main body 521.

To accommodate the shape of the assistance arm accommodation chamber 250, an angle β between the axis of the clamping assistance member 510 and the axis of the clamping assistance arm 520 ranges 120°-150°. As shown in FIG. 16, in accordance with the first implementation manner of the clamping assistance device 500, an angle β between the clamping assistance member 510 and the clamping assistance arm 520 is 120°. As shown in FIG. 17, in accordance with the second implementation manner of the clamping assistance device 500, angles β between multiple rod-shape clamping assistance member 510 and the clamping assistance arm 520 are all 140°. It is understood that, in other embodiments, if the clamping assistance arm 520 and the clamping assistance member 510 are made integrally using a flexible material, when the clamping assistance member 510 is axially accommodated in the assistance arm accommodation chamber 250 together with the clamping assistance arm 520, due to the angle between the distal chamber 251 of the assistance arm accommodation chamber 250 and the proximal chamber 252, the angle between the axis of the clamping assistance member 510 and the axis of the clamping assistance arm 520 ranges 120°-150°.

Figure 24:
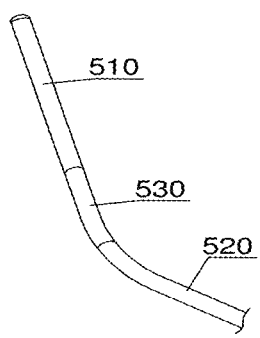
FIG. 24 is a schematic structural view of the clamping assistance device of the artificial chordae tendineae implantation system in accordance with the fourth implementation manner of the embodiments of the present disclosure.

Referring to FIG. 24, in accordance with the fourth implementation manner of the clamping assistance device 500, to enhance the supporting force to the leaflet by the clamping assistance member 510, particularly a lifting member 530 for supporting the clamping assistance member 510 and lifting the leaflet is disposed between the clamping assistance member 510 and the clamping assistance arm 520. The lifting member 530 is accommodated in the distal chamber 251 of the assistance arm accommodation chamber 250. A hardness of the lifting member 530 is larger than a hardness of the clamping assistance member 510 but smaller than a hardness of the clamping assistance arm 520. As such, when the clamping assistance member 510 passes out of the opening 260 of the pushing device 200 and contacts the leaflet, the lifting member 530 is located at the lower surface of the leaflet and lifts the leaflet, because the clamping assistance member 510 has flexibility, the lifting member 530 may move upwardly and downwardly together with the flapping of the leaflet, and because the lifting member 530 has a higher hardness, a more efficient support can be provided for the leaflet. In this embodiment, because the lifting member 530 with a higher hardness may not smoothly pass through the assistance arm accommodation chamber 250, particularly the assistance arm accommodation chamber 250 is a straight chamber body disposed obliquely in the pushing shaft 210; or as shown in FIG. 21, particularly the assistance arm accommodation chamber 250 includes a distal chamber 251 and a proximal chamber 252, the proximal chamber 252 is substantially parallel to the axis of the pushing shaft 210, an angle γ between the distal chamber 251 and the proximal chamber 252 ranges 120°-150°, and the lifting member 530 is accommodated in the distal chamber 251. In this embodiment, in order to accommodate the lifting member 530 in the pushing shaft 210, a split-type design of the pushing shaft 210 is needed, i.e., the pushing shaft 210 includes two tubular bodies having substantially semi-circular cross-sections that are opposed to each other, and in the production assembly, the clamping assistance arm 520, the lifting member 530, and the clamping assistance member 510 are first disposed together in the assistance arm accommodation chamber 250 of one of the tubular bodies, then the other half tubular body is docked and fixed together with the tubular body.

The clamping assistance member 510 is made of a biocompatible material opaque to X-rays, such as stainless steel, nickel titanium alloy or the like, and a nickel titanium alloy is used in this embodiment. In the prior art, before the clamping device clamps the leaflet, the relative position between the clamping device and the leaflet cannot be determined by methods such as X-rays that require a lower level of operation, and must rely on the accurate ultrasonographic guidance to move the clamping device to a suitable position, and the flapping state of the leaflet is monitored by ultrasonography, the relative movement between the distal clamp and the proximal clamp is quickly driven to clamp the leaflet when the leaflet pulsates near the clamping device. Ultrasonography imposes a higher requirement on the operational techniques and analytical abilities of cardiac ultrasonographic images of a doctor, causing a higher surgical difficulty and a prolonged surgical time, thereby increasing the risk of complications. Because the clamping assistance member 510 is made of a material opaque to X-rays, after the clamping assistance member 510 contacts the leaflet, the flexible or elastic clamping assistance member 510 generates corresponding oscillations accompanying the amplitude of the movement of the leaflet. As such, before the clamping device 300 clamps the leaflet, the operator may quickly and accurately determine the position of the leaflet by X-rays, so as to operate the clamping device 300 to clamp the leaflet more quickly and accurately, thereby reducing the surgical cost and increasing the surgery success rate.

Figure 25:
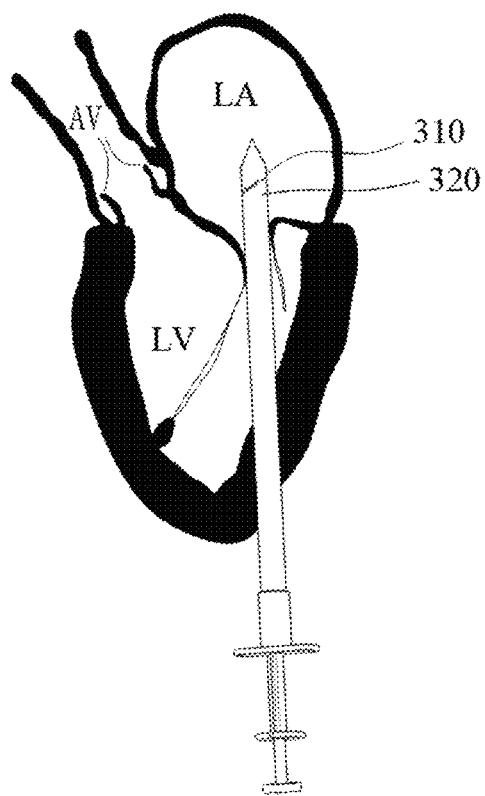
FIG. 25 to FIG. 31 are schematic procedural views of using the artificial chordae tendineae implantation system of the embodiments of the present disclosure to implant artificial chordae tendineae.

The following is an example of chordae tendineae implantation to a posterior leaflet of a mitral valve, for illustrating the implementation process of the artificial chordae tendineae implantation system:

At first step: referring to FIG. 25, the artificial chordae tendineae implantation system is pushed into the left ventricle, and the artificial chordae tendineae implantation system is pushed further till the distal clamp 310 and the proximal clamp 320 of the clamping device 300 are both located inside the left atrium.

Figure 26:
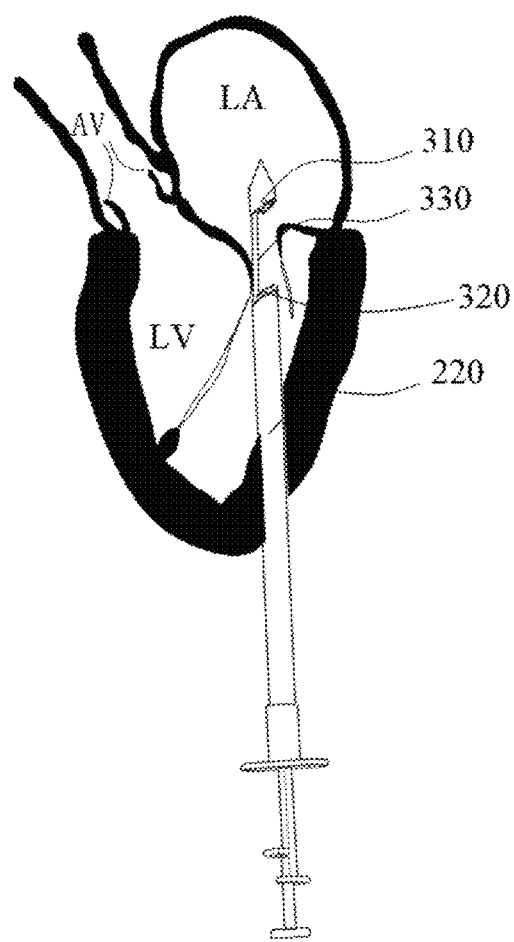

At second step: referring to FIG. 26, the pushing shaft 210 is retracted towards the proximal end or the clamping push rod 330 is pushed towards the distal end, causing the proximal clamp 320 disposed at the distal end of the pushing shaft 210 to be separated from the distal clamp 310 disposed at the distal end of the clamping push rod 330, at this time a leaflet accommodation space is formed between the proximal clamp 320 and the distal clamp 310.

Figure 27:
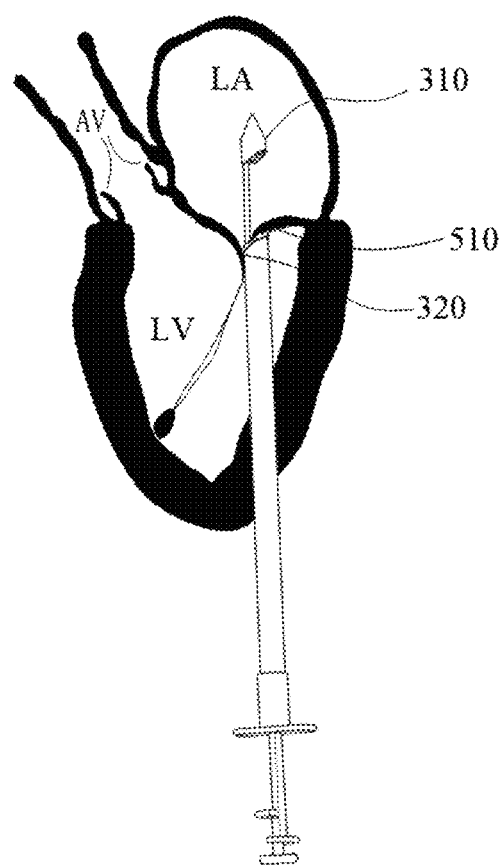

At third step: referring to FIG. 27, the fourth handle 501 is pushed towards the distal end, and the fourth handle 501 drives the clamping assistance arm 520 to push the clamping assistance member 510 to pass through from the opening 260, at this time the clamping assistance member 510 supports the lower surface of the leaflet to cooperatively stabilize the flapping leaflet; keeping the relative positions of the first handle 201, the second handle 301, and the fourth handle 501 unchanged, slowly moving the artificial chordae tendineae implantation system towards the proximal end, till the leaflet enters into the leaflet accommodation space formed between the proximal clamp 320 and the distal clamp 310, and the clamping assistance member 510 may provide certain support for the leaflet.

Figure 28A:
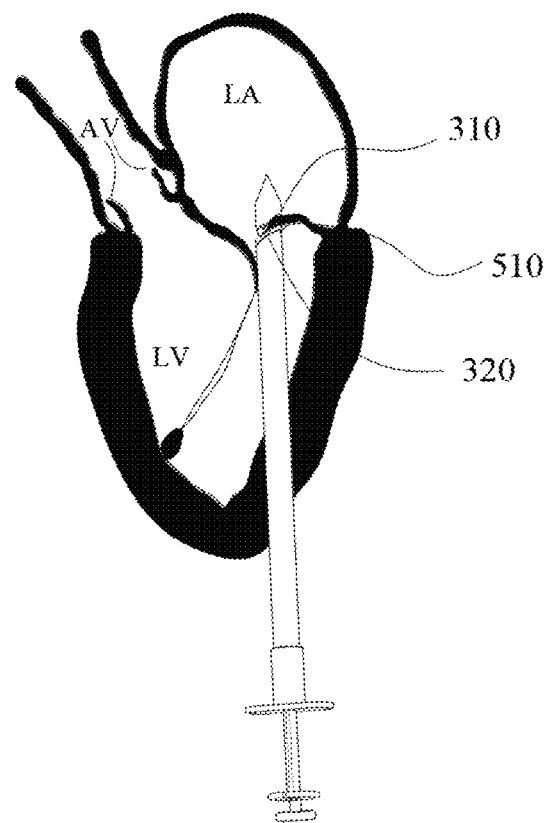
Figure 28B:
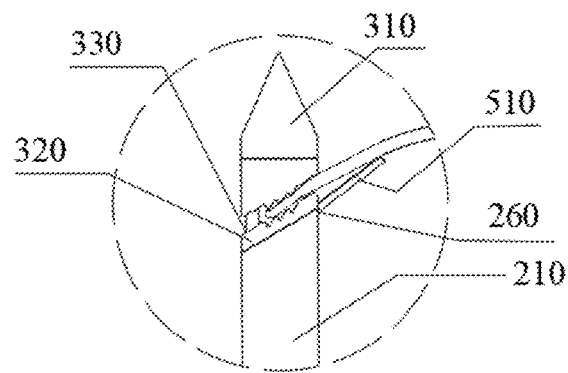

At fourth step: referring to FIG. 28A and FIG. 28B, slightly moving the distal end of the artificial chordae tendineae implantation system, till the leaflet edge contacts the clamping push rod 330, at this time retracting the second handle 301 towards the proximal end, driving the distal clamp 310 to move towards the proximal clamp 320 till the distal clamp 310 and the proximal clamp 320 are closed and the leaflet is clamped.

At fifth step: pushing the third handle 401 towards the distal end, driving the puncture needle 410 to move towards the distal end along the axial direction of the pushing shaft 210, i.e., the puncture needle 410 moves towards the distal clamp 310, till the puncture needle 410 passes through the leaflet and forms a fixed connection with the fixing member 120 of the artificial chordae tendinea 100.

Figure 29:
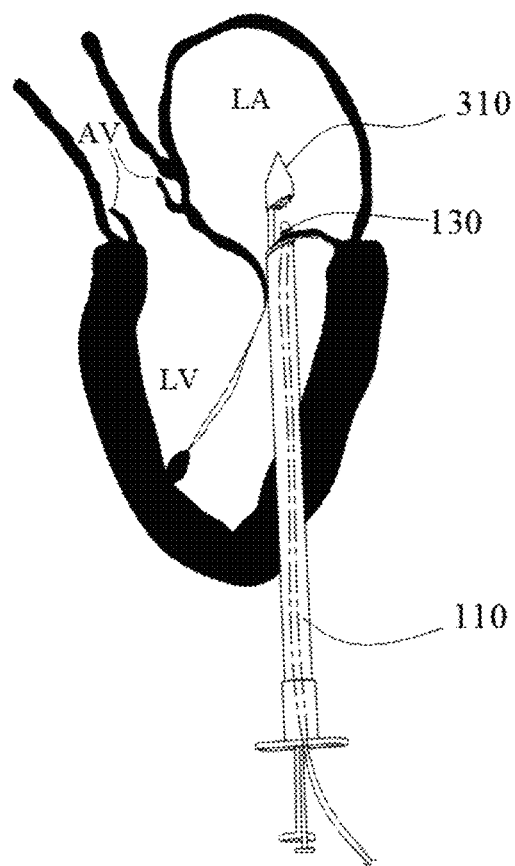
Figure 30:
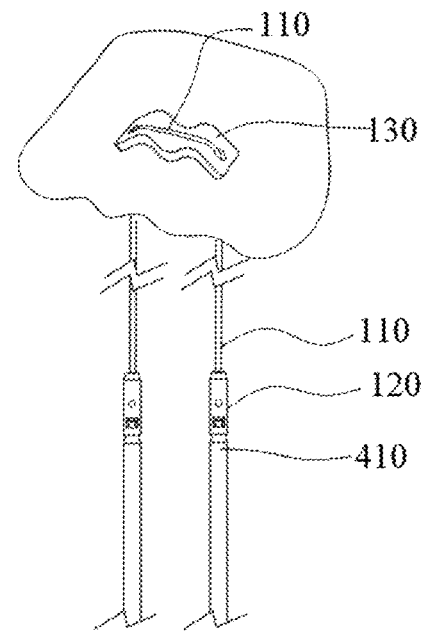

At sixth step: referring to FIG. 29, the third handle 401 is retracted, making the puncture needle 410 to drive the fixing member 120 of the artificial chordae tendinea 100, the chordae tendinea main body 110 connected with the fixing member 120 to successively pass through the leaflet. And the anti-slip member 130 is pulled out of the clamping surface 311 of the distal clamp 310, the fitting surface of the anti-slip member 130 (i.e., the lower surface) contacts the upper surface of the leaflet, meanwhile part of the chordae tendinea main body 110 presses the upper surface of the anti-slip member 130 to make it fit the leaflet (as shown in FIG. 30). At this time, the point contact between the artificial chordae tendinea 100 and the leaflet is converted into the face contact between the anti-slip member 130 and the leaflet, thereby efficiently reducing the risk of tearing the leaflet.

Figure 31:
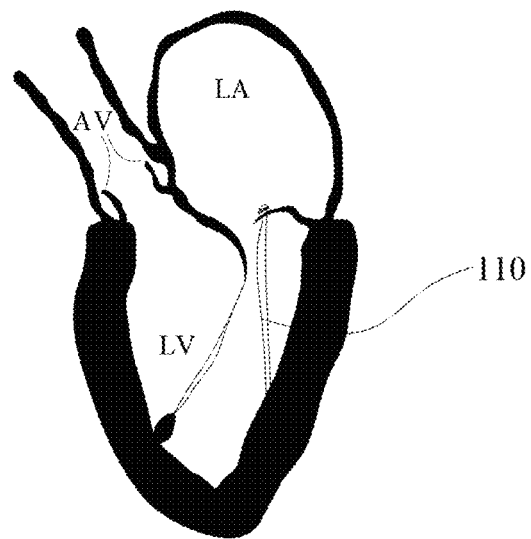

At seventh step: continuously retracting the third handle 401 till the fixing member 120 is retracted from the proximal end of the pushing shaft 120, then retracting the fourth handle 501, driving the clamping assistance member 510 to retract back to the assistance arm accommodation chamber 250, retracting the artificial chordae tendineae implantation system, and adjusting the length of the chordae tendinea main body 110 remaining in the heart, fixing both ends of the chordae tendinea main body 110 on the ventricular wall (as shown in FIG. 31).

During the fourth step as discussed above, after the leaflet is clamped by the clamping device 300, if the clamping position is found to be not ideal, the relative position between the distal clamp 310 and the proximal clamp 320 may be fine adjusted to create a certain distance between the distal clamp 310 and the proximal clamp 320, then the leaflet is clamped again; during the fine adjusting process, because the clamping assistance device 500 below the leaflet has a certain supporting for the leaflet, thereby preventing the leaflet from slipping off the clamping device 300.

The artificial chordae tendineae implantation system of the present disclosure has at least the following advantages over the prior art:

After the leaflet is clamped by the distal clamp and the proximal clamp, the clamping assistance member at the distal end of the clamping assistance arm may support the lower surface of the leaflet, to cooperatively clamp the flapping leaflet. After the leaflet is clamped by the clamping device, if the clamping position needs to be fine adjusted, the clamping assistance device below the leaflet has a supporting for the leaflet, and could efficiently prevent the leaflet from slipping off the clamping device.

Figure 32:
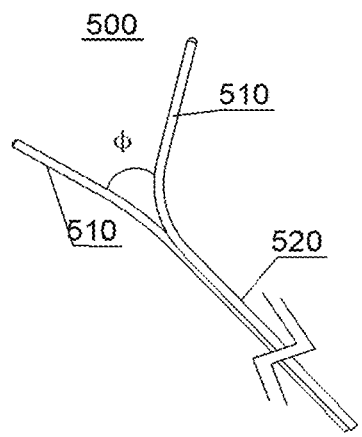
FIG. 32 and FIG. 33 are schematic structural views of the clamping assistance device of the artificial chordae tendineae implantation system in accordance with the fifth and sixth implementation manners of the embodiments of the present disclosure.
Figure 33:
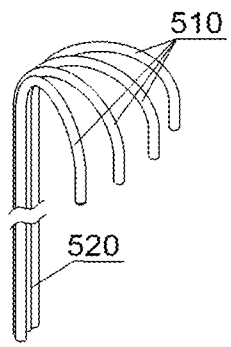

The clamping assistance device 500 may be improved further. As shown in FIG. 32 and FIG. 33, the fifth and the sixth implementation manners of the clamping assistance device 500 are basically the same as the first to the fourth implementation manners of the clamping assistance device 500, the differences are: the clamping assistance member 510 is a deformed structure composed of a plurality of support rods. The deformed structure is a Y-shape structure or an umbrella structure. The deformed structure after contracting and deforming is accommodated together with the clamping assistance arm 520 in the pushing shaft 210. Specifically, the deformed structure is an open Y-shape structure or an umbrella structure composed of a plurality of support rods. For facilitating the pushing in the pushing shaft, the clamping assistance member 510 has a compressed state and a stretched state in a natural state. The clamping assistance member 510 in the compressed state, can be accommodated and pushed in the assistance arm accommodation chamber 250 of the pushing shaft 210; when the clamping assistance member 510 passes through the opening 260 that is disposed on the clamping surface of the proximal clamp 320, the side wall of the pushing shaft 210, or the side wall of the proximal clamp 320, converts to the stretched state, and may support the lower surface of the leaflet and stabilize the flapping leaflet for facilitating the puncturing.

Referring to FIG. 32, in accordance with the fifth implementation manner of the clamping assistance device 500, the clamping assistance device 500 has a Y-shape structure formed by two support rods. The distal end of each support rod is a smooth structure, such as the structure of a round head, without defects like burrs, edges, corners. An angle φ between the two support rods ranges 20°-150°, particularly 60°-90°, so as to provide stable support to the leaflet without affecting the clamping assistance member 510 retracting towards the proximal end till inside the pushing shaft 210. Since the support rods have flexibility and elasticity, the clamping assistance member 510 can be folded and accommodated in the lumen of the pushing shaft 210. When pushed out of the pushing shaft 210, the two support rods due to their own flexibility and/or elasticity will return to a Y-shape having a certain angle and support the leaflet.

Correspondingly, at least two openings 260 are disposed on the clamping surface 321 of the proximal clamp 320, the side wall of the pushing shaft 210 or the side wall of the proximal clamp 320, each opening 260 is through connected with the assistance arm accommodation chamber 250, the clamping assistance member 510 passes out of at least one of the openings 260.

In usage, first the clamping assistance member 510 is retracted in advance to the proximal clamp 320 or the pushing shaft 210, the clamping assistance arm 520 is accommodated in the assistance arm accommodation chamber 250 of the pushing shaft 210, and the proximal end of the clamping assistance arm 520 passes out of the proximal end of the pushing shaft 210. When the fourth handle 501 on the proximal end of the clamping assistance arm 520 is driven along the axial direction of the pushing shaft 210 towards the distal end, the clamping assistance member 510 may be smoothly pushed out of the opening 260, and converts to the stretched state in the natural state (i.e., restoring to the Y-shape) due to its own flexibility and/or elasticity, the clamping assistance member 510 after contacting the lower surface of the leaflet provides support for the leaflet; when the clamping assistance arm 520 is pulling along the axial direction of the pushing shaft 210 towards the proximal end, the clamping assistance member 510 is folded and pulled back to the assistance arm accommodation chamber 250 of the pushing shaft 210. The clamping assistance arm 520 and the clamping assistance member 510 may be integrally formed, the clamping assistance arm 520 and the clamping assistance member 510 may be separately formed and then connected together.

Referring to FIG. 33, in accordance with the sixth implementation manner of the clamping assistance device 500, it is understood that, the clamping assistance member 510 of the clamping assistance device 500 is an umbrella structure composed of a plurality of support rods. The pushing shaft 210 may be provided with only one assistance arm accommodation chamber 250, at least two clamping assistance devices 500 are simultaneously insertedly mounted within the assistance arm accommodation chamber 250. That is, multiple independent clamping assistance members 510 and clamping assistance arm 520 connected with them are provided. Multiple clamping assistance members 510 pass out from the same opening 260, at this time a plurality of support rods forming the clamping assistance member 510 have a certain angle between them and form an umbrella structure. The umbrella structure supports the lower surface of the leaflet, and provides more efficient support for the leaflet. In this embodiment, the plurality of support rods forming the clamping assistance arm 520 may be fixed together between them by a limiting member like a hoop or an outer sleeve; the plurality of support rods may not be fixed with each other by a limiting member, and only the wall surface of the assistance arm accommodation chamber 250 restricts the radial deviation between the plurality of the clamping assistance arms 520. In addition, the axial movement of each support rod can be individually controlled to adjust the relative position between each support rod and the leaflet to accommodate the structures of the leaflets in different shapes for achieving a better supporting effect. It is also understood that, in other embodiments, the plurality of support rods that form the clamping assistance member 510 may also pass through different openings 260 respectively.

It is understood that, in other embodiments, the end of the clamping assistance device 500 in a Y-shape structure or an umbrella structure may roll towards the proximal end of the clamping assistance arm 520, and the clamping assistance member 510 rolls towards one side of the clamping assistance arm 520 to from a recessed area, as shown in FIG. 33. At this time, because the end of each clamping assistance member 510 rolls inwardly towards the proximal end of the clamping assistance arm 520, thereby preventing the end of the clamping assistance member 510 from stabbing the leaflet or the ventricular wall.

The clamping assistance device 500 in accordance with the fifth and the sixth implementation manner has the following beneficial technical effects over the prior art:

The clamping assistance device is a Y-shape or an umbrella shape, the contact surface between the clamping assistance member and the leaflet is a plane formed by the clamping assistance member, as such, the contact area between the clamping assistance device and the leaflet is larger, with stronger support; and better fitting the leaflet and more efficiently supporting the leaflet.

Figure 34:
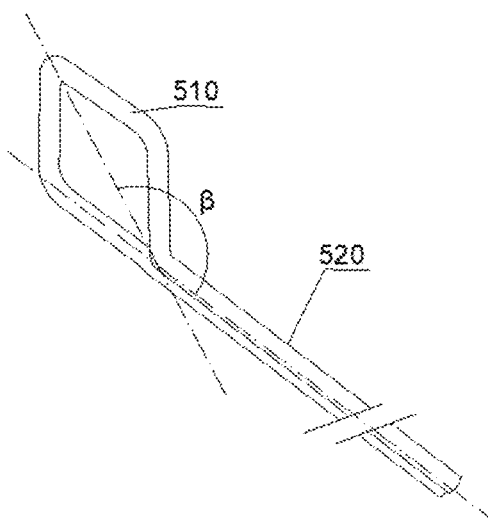
FIG. 34 to FIG. 37 are schematic structural views of the clamping assistance device of the artificial chordae tendineae implantation system in accordance with the seventh to tenth implementation manners of the embodiments of the present disclosure.
Figure 35:
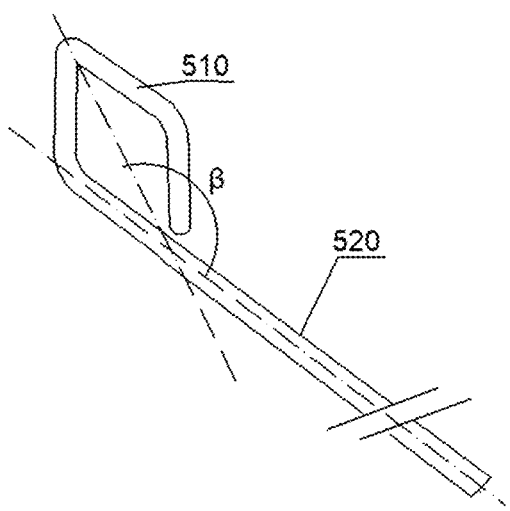
Figure 36:
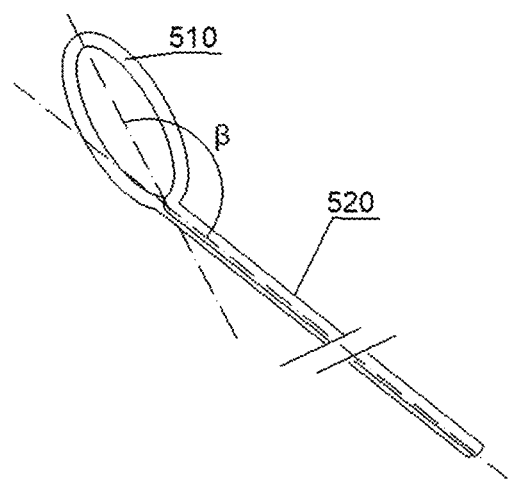

The clamping assistance device 500 may be further improved:

Referring to FIG. 34 to FIG. 36, the clamping assistance device 500 in accordance with the seventh to the ninth implementation manners is basically the same as the clamping assistance device 500 in accordance with the first to the fourth implementation manners, the differences are: the clamping assistance device 500 in accordance with the seventh to the ninth implementation manners have the clamping assistance member 510 located at the distal end of the clamping assistance arm 520 in a deformed structure formed by a plurality of support rods. The deformed structure after contracting and deforming is accommodate together with the clamping assistance arm 520 in the pushing shaft 210. In this embodiment the deformed structure is a closed loop structure, and the closed loop structure may be a circle, a diamond, an ellipse, a pear, a polygon, or other irregular shape that may form a closed structure.

Figure 37:
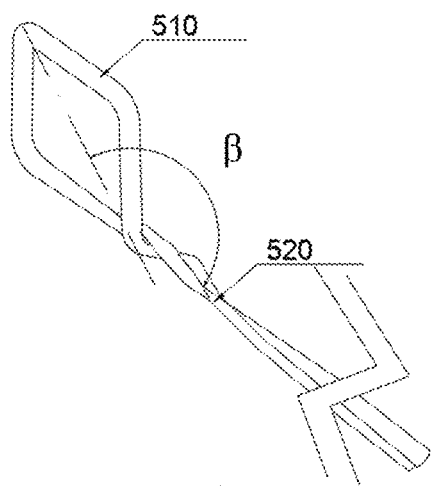

Referring to FIG. 37, in accordance with the tenth implementation manner of the clamping assistance device 500, the proximal ends of the two support rods are particularly cross set, i.e., the proximal end of the clamping assistance member 510 is a twist-type structure. As such, the stress point area between the clamping assistance member 510 and the clamping assistance arm 520 may be increased, thereby preventing the deformation of the joint between the clamping assistance member 510 and the clamping assistance arm 520 caused by the flapping of the leaflet, further enhancing the supporting for the leaflet by the clamping assistance member 510.

Figure 38:
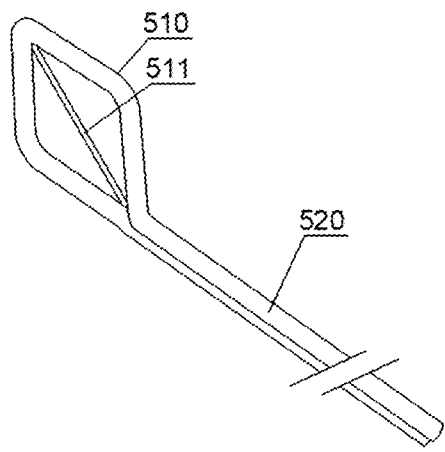
FIG. 38 is a schematic structural view of the clamping assistance device of the artificial chordae tendineae implantation system in accordance with the eleventh implementation manner of the embodiments of the present disclosure.

Referring to FIG. 38, in accordance with the eleventh implementation manner of the clamping assistance device 500, at least a connecting rod 511 having flexibility and/or elasticity is disposed between the support rods of the closed loop structure, to enhance the self-stability of the close loop structure, further enhancing the supporting force for the leaflet by the clamping assistance member 510. The clamping assistance member 510 includes two support rods and the connecting rod connecting between the two support rods. Each support rod corresponds to an opening 260, and a length of the support rod is equal to or slightly larger than a length of the opening 260.

It is understood that, in other embodiments, when the closed loop structure is provided with a plurality of support rods and connecting rods, the closed loop structure may also form a sheet structure or a mesh structure.

It can also be understood that, in other embodiments, the mesh structure may be heat-treated, such that the mesh structure may form a stretchable disc-shaped structure (similar to a single disc occluder in the prior art). The disc-shaped structure can be further heat-treated to form a columnar, nested, oblate, or the like structure. As long as the clamping assistance member 510 is made of a shape memory material, it can be delivered in the assistance arm accommodation chamber 250 of the pushing shaft 210, and then passes through the opening 260 to restore to the natural stretched state, contacts the lower surface of the leaflet and provides support for the leaflet.

Figure 39A:
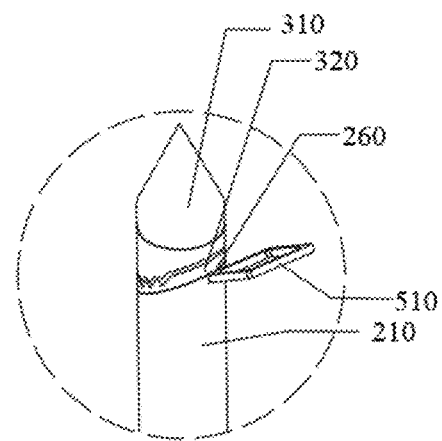
FIG. 39A and FIG. 39B are schematic views of the clamping assistance device of the artificial chordae tendineae implantation system in accordance with the eleventh implementation manner of the embodiments of the present disclosure and illustrate the lifting of the leaflet by the clamping assistance device.
Figure 39B:
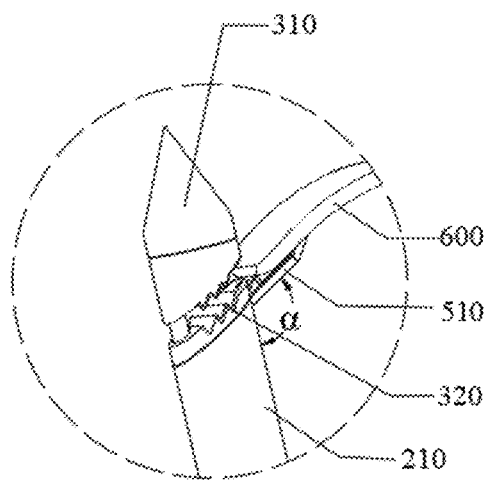

Because an angle α between the opening 260 of the assistance arm accommodation chamber 250 and the axial direction of the pushing shaft 210 ranges 120°-150°, when the clamping assistance member 510 located at the distal end of the clamping assistance arm 520 is pushed out of the opening 260, the clamping assistance member 510 restores to the stretched state, and an angle between the clamping assistance member 510 and the pushing shaft 210 ranges 120°-150° (as shown in FIG. 39A). As such, the clamping assistance member 510 contacts the lower surface of the leaflet 600 (as shown in FIG. 39B), and the contact surface has a larger area, consequently the clamping assistance device of this embodiment provides a more stable supporting force.

Figure 40A:
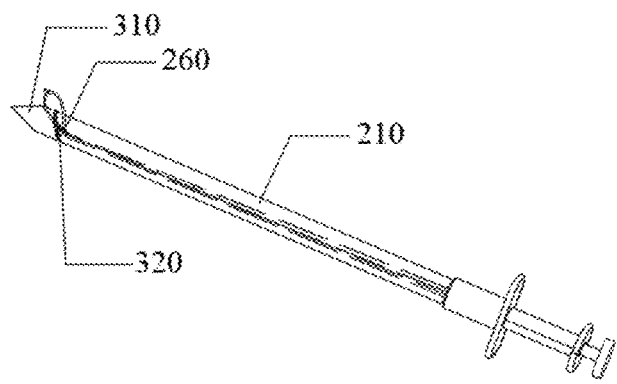
FIG. 40A to FIG. 40C are schematic structural views of the clamping assistance device of the artificial chordae tendineae implantation system in accordance with the twelfth implementation manner of the embodiments of the present disclosure.
Figure 40B:
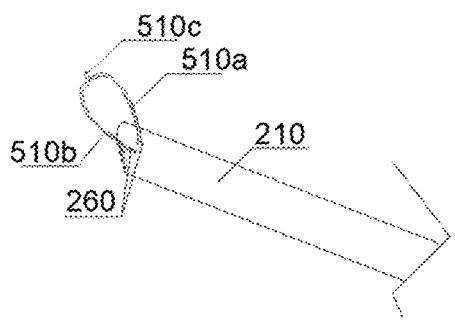
Figure 40C:
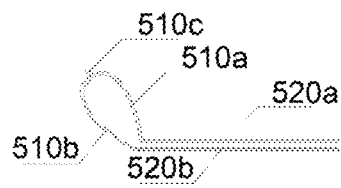

Referring to FIG. 40A to FIG. 40C, in accordance with the twelfth implementation manner of the clamping assistance device 500, the differences from the clamping assistance device 500 according to the tenth implementation manner are: the clamping assistance arm 520 is movably insertedly mounted within the assistance arm accommodation chamber 250, the clamping assistance member 510 is disposed at the distal end of the clamping assistance arm 520. The clamping assistance member 510 includes two support rods 510a and 510b, and a connecting rod 510c that connects between the two support rods 510a and 510b. At least two openings 260 are disposed on the clamping surface 321 of the proximal clamp 320, the side wall of the pushing shaft 210, or the side wall of the proximal clamp 320, each of the openings 260 is through connected to the assistance arm accommodation chamber 250. For example, two openings 260 may be disposed simultaneously on the side wall of the pushing shaft 210, or two openings 260 may be disposed simultaneously on the clamping surface 321 of the proximal clamp 320, or two openings 260 may be disposed simultaneously on the side wall of the proximal clamp 320. Each of the support rods 510a and 510b forming the clamping assistance member 510 corresponds to an opening 260, a length of the support rods 510a and 510b is equal to or slightly larger than a length of the opening 260. That is, the distal ends of the support rods 510a and 510b pass through out of one of the openings 260 respectively and are connected by the connecting rod 510c to each other.

The two support rods 510a and 510b and the connecting rod 510c are heat-treated in advance to form a circular, diamond, pear, polygon or other substantially closed loop structure.

Before using, the clamping assistance arm 520 is insertedly mounted within the assistance arm accommodation chamber 250, the support rods 510a and 510b are insertedly mounted within the assistance arm accommodation chamber 250 at the opening 260, and the connecting rod 510c fits the outer surface of the pushing shaft 210 or the proximal clamp 320. It is understood that, in other embodiments, the outer surface of the proximal clamp 320 may be provided with indentations for accommodating the connecting rod.

In using, by pushing the fourth handle 501 at the proximal end of the clamping assistance arm 520, the clamping assistance arm 520 moves axially towards the distal end, making the support rods 510a and 510b to gradually pass out completely from the opening 260 of the pushing shaft 210 or the proximal clamp 320, till the support rods 510a and 510b and the connecting rod 510c restore to the natural state after the heat-treated. That is, the entire clamping assistance member 510 restores to the closed loop state of the stretched state. At this time, the support rods 510a and 510b and the connecting rod 510c form a plane, the plane contacts the lower surface of the leaflet and lifts the leaflet to provide the supporting force.

It is understood that, in this embodiment, if only one clamping assistance arm 520 is used, transition sections 520a and 520b should be provided between the distal end of the clamping assistance arm 520 and the proximal ends of the two support rods 510a and 510b, respectively. A length of the transition sections 520a and 520b is greater than or equal to the length of the support rods 510a and 510b. As such, after driving the fourth handle 501 at the proximal end of the clamping assistance arm 520, the transition sections 520a and 520b enter into the opening 260 and fully push out the support rods 510a and 510b, the support rods 510a and 510b and the connecting rod 510c restore to the natural state after the heat-treated.

It is also understood that, in other embodiments, two clamping assistance arms 520 may be used, a support rod is disposed at the distal end of each clamping assistance arm 520. Two support rods 510a and 510b are connected by a connecting rod 510c. As such, after driving the fourth handle 501 at the proximal ends of the two clamping assistance arms 520, the two clamping assistance arms 520 fully push out the two support rods 510a and 510b, the support rods 510a and 510b and the connecting rod 510c restore to the natural state after the heat-treated. It is understood that, in other embodiments, if the hardness of the clamping assistance arm 520 itself is lower, there is no need to dispose transition sections 520a and 520b, and may merely rely on the clamping assistance arm 520 to push the support rod out of the opening 260.

The clamping assistance device 500 according to the twelfth implementation manner has at least the following advantages over the prior art:

The contact area between the clamping assistance member and the leaflet is larger, and, when the clamping assistance member is subject to the force of the leaflet, a single stress point between the support rod and the clamping assistance arm is converted into the stress surface between the two support rods and the two openings, dispersing the force, thereby providing greater supporting force and better conforming to the amplitude of the movement of the leaflet, lifting the leaflet.

Overall, the artificial chordae tendineae implantation system of the present disclosure adds the clamping assistance device to the artificial chordae tendineae implantation system. The clamping assistance arm of the clamping assistance device is movably insertedly mounted within the pushing shaft. The clamping assistance member passes through out of the distal end of the pushing shaft or the distal end of the clamping device. After the leaflet is clamped by the distal clamp and the proximal clamp, the clamping assistance member may support the lower surface of the leaflet, lifts the leaflet towards the atrial side, thereby reducing the amplitude of the movement of the leaflet and cooperating with the clamping device to clamp the flapping leaflet. Moreover, after the clamping assistance device supports the lower surface of the leaflet, if the operator finds that the clamping position is not ideal, the clamping device can be fine adjusted, and during the fine adjustment process, the support of the clamping assistance device prevents the leaflet from slipping off the clamping device.

The foregoing implementations are merely specific embodiments of the present disclosure, and are not intended to limit the protection scope of the present disclosure. It should be noted that any variation or replacement readily figured out by persons skilled in the art within the technical scope disclosed in the present disclosure shall all fall into the protection scope of the present disclosure. Therefore, the protection scope of the present disclosure shall be subject to the protection scope of the claims.

What is claimed is:

1. An artificial chordae tendineae implantation system, comprising a clamping device, a puncture device, and a pushing device,
wherein
the pushing device comprises a pushing shaft, the puncture device and the clamping device are respectively movably insertedly mounted within the pushing shaft, the clamping device accommodates an artificial chordae tendinea, the implantation system further comprises at least one clamping assistance device;
the clamping device comprises a clamping push rod, and a distal clamp and a proximal clamp for cooperatively clamping a leaflet, the proximal clamp is disposed at a distal end of the pushing shaft, the distal clamp is disposed at a distal end of the clamping push rod;
the at least one clamping assistance device comprises a clamping assistance arm movably insertedly mounted within the pushing shaft and a clamping assistance member disposed on a distal end of the clamping assistance arm;
the clamping assistance member is made of an elastic and/or flexible material and deformable, the clamping assistance member and the clamping assistance arm are accommodated together in the pushing shaft;
the clamping assistance arm pushes the clamping assistance member out of the distal end of the pushing shaft to support the leaflet, the clamping assistance member is configured to cooperate with the clamping device to clamp the leaflet, to allow the leaflet to be clamped between the distal clamp and the proximal clamp, and
an assistance arm accommodation chamber is disposed within the pushing shaft along an axial direction of the pushing shaft, the assistance arm accommodation chamber comprises a distal chamber and a proximal chamber, the proximal chamber is substantially parallel to an axis of the pushing shaft, and an angle between the distal chamber and the proximal chamber ranges from 120° to 150°.

2. The artificial chordae tendineae implantation system according to claim 1, wherein an angle between an axis of the clamping assistance member and an axis of the clamping assistance arm ranges from 120° to 150°.

3. The artificial chordae tendineae implantation system according to claim 1, wherein the clamping assistance member and the clamping assistance arm are integrally formed, or are detachably or non-detachably connected.

4. The artificial chordae tendineae implantation system according to claim 1, wherein the clamping assistance arm is a rod-shape or a tubular structure made of a hard material.

5. The artificial chordae tendineae implantation system according to claim 1, wherein a lifting member is disposed between the clamping assistance member and the clamping assistance arm, the lifting member is accommodated in the distal chamber of the assistance arm accommodation chamber, a hardness of the lifting member is greater than a hardness of the clamping assistance member and less than a hardness of the clamping assistance arm.

6. The artificial chordae tendineae implantation system according to claim 1, wherein the clamping assistance member is at least partially made of a material opaque to X-rays.

7. The artificial chordae tendineae implantation system according to claim 1, wherein the clamping assistance member is a L-shaped rod-shape structure formed by one support rod, the clamping assistance member and the clamping assistance arm are accommodated together in the pushing shaft.

8. The artificial chordae tendineae implantation system according to claim 1, further comprising the artificial chordae tendinea, wherein the artificial chordae tendinea comprises a flexible chordae tendinea main body, the chordae tendinea main body comprises a first end and a second end opposite to the first end, the first end and/or the second end are connected with a fixing member, a puncture connecting member is disposed on one side of the fixing member facing away from the chordae tendinea main body, and the puncture connecting member is coupled with a puncture needle of the puncture device.

9. The artificial chordae tendineae implantation system according to claim 8, wherein an anti-slip member is sleeved on the chordae tendinea main body, the anti-slip member is provided with a fitting surface configured to fit the leaflet, the anti-slip member slides along an axial direction of the chordae tendinea main body.

10. The artificial chordae tendineae implantation system according to claim 1, wherein an opening is provided on a clamping surface disposed at a distal end of the proximal clamp, a side wall of the pushing shaft or a side wall of the proximal clamp, the opening is through connected with the assistance arm accommodation chamber, and the clamping assistance member passes through the opening.

11. The artificial chordae tendineae implantation system according to claim 10, wherein at least one additional opening is provided on the clamping surface disposed at the distal end of the proximal clamp, the side wall of the pushing shaft or the side wall of the proximal clamp, the at least one additional opening is through connected with the assistance arm accommodation chamber, the clamping assistance member passes through the at least one additional opening.

12. The artificial chordae tendineae implantation system according to claim 11, wherein the clamping assistance member comprises two support rods and a connecting rod connecting between the two support rods, each support rod corresponds to one of the openings, a length of each support rod is equal to or slightly larger than a length of the respective opening.

13. The artificial chordae tendineae implantation system according to claim 10, wherein an artificial chordae tendinea channel is disposed within the clamping push rod along an axial direction of the clamping push rod, an artificial chordae tendineae accommodation chamber is disposed inside the distal clamp, a distal end of the artificial chordae tendineae accommodation chamber is through connected with a clamping surface of the distal clamp, the artificial chordae tendinea channel is connected to the artificial chordae tendineae accommodation chamber, the artificial chordae tendineae is accommodated in the artificial chordae tendinea channel and the artificial chordae tendineae accommodation chamber.

14. The artificial chordae tendineae implantation system according to claim 10, wherein a clamping surface of the distal clamp is provided with an accommodation indentation of an anti-slip member for accommodating the artificial chordae tendinea, the accommodation indentation is radially connected with an artificial chordae tendineae accommodation chamber.

15. The artificial chordae tendineae implantation system according to claim 14, wherein the clamping surface of the distal clamp is provided with a fixing chamber for accommodating a fixing member of the artificial chorda tendinea, the fixing chamber is axially connected with the artificial chordae tendineae accommodation chamber, the fixing chamber is radially connected with the accommodation indentation.

16. The artificial chordae tendineae implantation system according to claim 10, wherein the clamping surface of the proximal clamp fits a clamping surface of the distal clamp, at least one of the clamping surfaces is provided with a clamping reinforcement member for reinforcing a clamping force.

* * * * *